(12) United States Patent
Golic et al.

(10) Patent No.: US 7,285,699 B2
(45) Date of Patent: Oct. 23, 2007

(54) ENDS-OUT GENE TARGETING METHOD

(75) Inventors: Kent G. Golic, Salt Lake City, UT (US); Wei J. Gong, Salt Lake City, UT (US)

(73) Assignee: Stowers Institute for Medical Research, Kansas City, MO (US)

( * ) Notice: Subject to any disclaimer, the term of this patent is extended or adjusted under 35 U.S.C. 154(b) by 129 days.

(21) Appl. No.: 10/434,668

(22) Filed: May 9, 2003

(65) Prior Publication Data

US 2004/0068761 A1    Apr. 8, 2004

Related U.S. Application Data

(60) Provisional application No. 60/416,561, filed on Oct. 7, 2002.

(51) Int. Cl.
*C12N 15/00* (2006.01)
(52) U.S. Cl. .......................................... 800/21; 800/22
(58) Field of Classification Search ..................... 800/8
See application file for complete search history.

(56) References Cited

U.S. PATENT DOCUMENTS 4,959,317 A   9/1990 Sauer
5,962,327 A   10/1999 Dujon et al.

OTHER PUBLICATIONS

Spradling AC, Gene disruptions in P transosable elements: an integral component of the *Drosophila* genome project, 1995, 92, pp. 10824-10830.*
Bellaiche Y, I-SceI endonuclease, a new tool for studying DNA double-strand break repair mechanims in *Drosophila*, 1999, Genetics, 152, pp. 1037-1044.*
Golic KG, Gene targeting by homologous recombination in *Drosophila*, 2000, Science, 288, pp. 2013-2018.*
Rong, Yikang S. et al., Gene Targeting by Homologous Recombination in *Drosophila*, 2000, Science, vol. 288, p. 2013-2018.
Hastings, P.J. et al., Ends-In vs. Ends-Out Recombination in Yeast, Jun. 16, 1993, Genetics, vol. 135, p. 973-980.
Bellaiche, Yohanns et al., I-SceI Endonuclease, a New Tool for Studying DNA Double-Strand Break Repair Mechanisms in *Drosophila*, Jul. 1999, Genetics, vol. 152, p. 1037-1044.
Rong, Yikang S. et al., Targeted mutagenesis by homologous recombination in *D. melanogaster*, 2002, Genes & Development, vol. 16, p. 1568-1581.
Schwartzberg, Pamela L. et al., Targeted gene disruption of the endogenous c-abl locus by homologous recombination with DNA encoding a selectable fusion protein, Apr. 1990, Proc. Natl. Acad. Sci. USA, vol. 87, p. 3210-3214.
Rong, Yikang S. et al., A Targeted Gene Knockout in *Drosophila*, Mar. 2001, Genetics, vol. 157, p. 1307-1312.
Golic, Kent G., Local Transposition of P Elements in *Drosophila melanogaster* and Recombination Between Duplicated Elements Using a Site-Specific Recombinase, Jun. 1994, Genetics, vol. 137, p. 551-563.

Ahmad, Kami et al., Telomere Loss in Somatic Cells of *Drosophila* Causes Cell Cycle Arrest and Apoptosis, Mar. 1999, Genetics, vol. 151, p. 1041-1051.
Fitzgerald, Daniel P. et al., Polycomb Group Repression Reduces DNA Accessibility, Oct. 2001, Molecular and Cellular Biology, vol. 21, p. 6585-6597.
Seum, Carole et al., Isolation of Su (var) 3-7 Mutations by Homologous Recombination in *Drosophila melanogaster*, Jul. 2002, Genetics, vol. 161, p. 1125-1136.
Golic, Mary M. et al., A Quantitative Measure of the Mitotic Pairing of Alleles in *Drosophila melanogaster* and the Influence of Structural Heterozygosity, May 1996, Genetics, vol. 143, p. 385-400.
Dale, Emily C. et al., Gene transfer with subsequent removal of the selection gene from the host genome, Dec. 1991, Proc. Natl, Acad. Sci USA, vol. 88, p. 10558-10562.
Bunting, Michaeline et al., Targeting genes for self-excision in the germ line, 1999, Genes & Development, 13, 1524-1528.
Siegal, Mark L. et al., Transgene Coplacement with High Efficiency Site-Specific Recombination with the Cre/IoxP System in *Drosophila*, Oct. 1996, Genetics, vol. 144, p. 715-726.
Bronson, Sarah K. et al., Altering Mice by Homologous Recombination Using Embryonic Stem Cells, Nov. 4, 1994, The Journal of Biological Chemistry, vol. 269, p. 27155-27158.
McCreath, K. J. et al., Production of gene-targeted sheep by nuclear transfer from cultured somatic cells, Jul. 29, 2000, Nature, vol. 405, p. 1066-1069 and supplement p. 1.
Sargent, R. Geoffrey et al., Repair of Site-Specific Double-Strand Breaks in a Mammalian Chromosome by Homologous and Illegitimate Recombination, Jan. 1997, Molecular and Cellular Biology, vol. 17, p. 267-277.
Liang, Feng et al., Homology-directed repair is a major doublestand break repair pathway in mammalian cells, Apr. 1998, Proc. Natl. Acad. Sci. USA, vol. 95, p. 5172-5177.
Cohen-Tannoudji, Michel et al., I-ScI-Induced Gene Replacement at a Natural Locus in Embryonic Stem Cells, Mar. 1998, Molecular and Cellular Biology, vol. 18, p. 1444-1448.
Belfort, Marlene et al., Homing endonucleases: keeping the house in order, 1997, Nucleic Acids Research, vol. 25, No. 17, p. 3379-3388.

(Continued)

*Primary Examiner*—Deborah Crouch
*Assistant Examiner*—David A. Montanari
(74) *Attorney, Agent, or Firm*—Polsinelli Shalton Flanigan Suelthaus PC

(57) ABSTRACT

A gene targeting method for use in a host organism whereby the host organism is transfected with an ends-out donor construct. Further transfecting the host organism with two transgenes expressing endonuclease and recombinase enzymes. The endonuclease and recombinase enzymes are used so that homologous recombination occurs between the DNA segment of the donor construct and a selected gene of the host organism, thus forming a host with containing the recombinogenic donor. The progeny of the host organism, which include the recombinogenic donor are then selected.

11 Claims, 5 Drawing Sheets

OTHER PUBLICATIONS

Nunes-Duby, Simone E. et al., Similarities and differences among 105 members of the Int family of site-specific recombinases, 1998, Nucleic Acids Research, vol. 26, No. 2, p. 391-406.

Catteruccia, Flaminia et al., Stable germline transformation of the malaria mosquito *Anopheles stephensi*, Jun. 2, 2000, Nature, vol. 405, p. 954-962.

Haren, L. et al., Integrating DNA: Transposases and Retroviral Integrases, 1999, Annu. Rev. Microbiol. vol. 53, p. 245-281.

Beall, Eileen L. et al., *Drosophila* P-element transposase is a novel site-specific endonuclease, 1997, Genes & Development, vol. 11, p. 2137-2151.

Polejaeva, Irina A. et al., Cloned pigs produced by nuclear transfer from adult somatic cells, Sep. 7, 2000, Nature, vol. 407, p. 88-90.

Dray, Tammy et al., Homology Requirements for Targeting Heterologous Sequences During P-Induced Gap Repair in *Drosophila melanogaster*, Oct. 1997, Genetics, vol. 147, p. 689-699.

Golic, Mary M. et al., FLP-mediated DNA mobilization to specific target sites in *Drosophila* chromosomes, 1997, Nucleic Acids Research, vol. 25, No. 18, p. 3665-3671.

Leung, W.-Y. et al., Gene targeting by linear duplex DNA frequently occurs by assimilation of a single strand that is subject to preferential mismatch correction, Jun. 1997, Proc. Natl., Acad. Sci. USA, vol. 94, p. 6851-6856.

Hasty, Paul et al., Target Frequency and Integration Pattern for Insertion and Replacement Vectors in Embryonic Stem Cells, Sep. 1991, Molecular and Cellular Biology, vol. 11, p. 4509-4517.

Thomas, Krik R. et al., Site-Directed Mutagenesis by Gene Targeting in Mouse Embryo-Derived Stem Cells, Nov. 6, 1987, Cell, vol. 51, p. 503-512.

Deng, Chuxia et al., Reexamination of Gene Targeting Frequency as a Function of the Extent of Homology between the Targeting Vector and the Target Locus, Aug. 1992, Molecular and Cellular Biology, vol. 12, No. 8, p. 3365-3371.

Klemenz, Roman et al., The white gene as a marker in a new P-element vector for gene transfer in *Drosophila*, 1987, Nucleic Acids Research, vol. 15, No. 10, p. 3947-3959.

Geyer, Pamela K. et al., Separate regulatory elements are responsible for the complex pattern of tissue-specific and developmental transcription of the yellow locus in *Drosophila melanogaster*, 1987, Genes & Development, vol. 1, p. 996-1004.

Rubin, Gerald M. et al., Vectors for P element-mediated gene transfer in *Drosophila*, 1983, Nucleic Acids Research, vol. 11, No. 18, p. 6341-6351.

Golic, Kent G. et al., The FLP Recombinase of Yeast Catalyzes Site-Specific Recombination in the *Drosophila* Genome, Nov. 3, 1989, Cell, vol. 59, p. 499-509.

Rubin, Gerald M. et al., Genetic Transformation of *Drosophila* with Transposable Element Vectors, Oct. 1982, Science, vol. 218, p. 348-353.

Orr-Weaver, Terry L. et al., Yeast transformation: A model system for the study of recombination, Oct. 1981, Proc. Natl. Acad. Sci. USA, vol. 78, No. 10, p. 6354-6358.

Thomas, Kirk R. et al., High-Fidelity Gene Targeting in Embryonic Stem Cells by Using Sequence Replacement Vectors, Jul. 1992, Molecular and Cellular Biology, vol. 12, p. 2919-2923.

Michiels, Frits et al., A 14 bp promoter element directs the testis specificity of the *Drosophila* β2 tubulin gene, 1989, The TMBO Journal, vol. 8, No. 5, p. 1559-1585.

Bonnner, J. Jose et al., The Use of Promoter Fusions in *Drosophila* Genetics: Isolation of Mutations Affecting the Heat Shock Response, Jul. 1984, Cell, vol. 37, p. 979-991.

Surosky, Richard T. et al., Construction of telocentric chromosomes in *Saccharomyces cerevisiae*, Apr. 1985, Proc. Natl. Acad. Sci. USA, vol. 82, p. 2106-2110.

Matzuk, Martin M. et al., α-Inhibin is a tumour-suppressor gene with gonadal specificity in mice, Nov. 26, 1992, Nature, vol. 360, p. 313-319.

Gu, Hua et al., Deletion of a DNA Polymerase β Gene Segment in T Cells Using Cell Type-Specific Gene Targeting, Jul. 1, 1994, Science, vol. 265, p. 103-106.

Meyers, Erik N. et al., An Fg18 mutant allelic series generated by Cre- and Flp-mediated recombination, Feb. 18, 1998, Nature Genetics, vol. 18, p. 138-141.

Mansour, Suzanne L. et al., Disruption of the proto-oncogene int-2 in mouse embryo-derived stem cells: a general strategy for targeting mutations to non-selectable genes, Nov. 24, 1988, Nature, vol. 336, p. 348-352.

Capecchi, Mario R., The New Mouse Genetics: Altering the Genome by Gene Targeting, Mar. 1989, Trends in Genetics, vol. 5, No. 3, p. 70-76.

Nancy L. Craig, The Mechanism of Conservative Site-Specific Recombination, 1988, Annu. Rev. Genet, vol. 22, p. 77-105.

Reznikoff, William S. et al., Tn5: A Molecular Window on Transposition, 1999, Biochemical and Biophysical Research Communication, vol. 266, p. 729-734.

Ivics, Zoltán et al., Genetic Application of Transposons and Other Repetitive Elements in Zebrafish, 1999, Methods in Cell Biology, vol. 60, p. 99-131.

Craig, Nancy L., Target Site Selection in Transposition, 1997, Annu. Rev. Biochem, vol. 68, p. 437-474.

Shulman, Mark J. et al., Homologous Recombination in Hybridoma Cells: Dependence on Time and Fragment Length, Sep. 1990, Molecular and Cellular Biology, p. 4466-4472.

Scheerer, Julia B. et al., Homology Dependence of Targeted Recombination at the Chinese Hamster APRT Locus, Oct. 1994, Molecular and Cellular Biology, vol. 14, p. 6663-6673.

Rothstein, Rodney, Targeting, Disruption, Replacement, and Allele Rescue: Integrative DNA Transformation in Yeast, 1991, Methods in Enzymology, vol. 194, p. 281-301.

Gloor, Gregory B., et al., Targeted Gene Replacement in *Drosophila* via P Element-Induced Gap Repair, 1991, Science, vol. 253, p. 1110-1117.

Hallet, Bernard et al., Transposition and site-specific recombination: adapting DNA cut-and-paste mechanism to a variety of genetic rearrangements, 1997, FEMS Microbiology Reviews, vol. 21, p. 157-178.

Hoess, R.H. et al., The Cre-lox Recombination System, 1990, Nucleic Acids and Molecular Biology, vol. 4, p. 99-109.

Müller, Ulrike, Ten years of gene targeting: targeted mouse mutants, from vector design to phenotype analysis, 1999, Mechanisms of Development, vol. 82, p. 3-21.

Weinberg, Eric S., Zebrafish genetics: Harnessing horizontal gene transfer, Mar. 26, 1998, vol. 8, No. 7, p. R244-247.

Sauer, Brian, Site-specific recombination: developments and applications, 1994, Current Opinion in Biotechnology, vol. 5, p. 521-527.

Cox, M. M., FLP site-specific recombination system of *Saccharomyces cerevisiae*, 1988, In Genetic Recombination, R. Kucherlapati and G. R. Smith, eds. (American Society for Microbiology, Washington D.C.), pp. 429-443.

Gong, Wei J. et al., Ends-out, or replacement, gene targeting in *Drosophila*, PNAS, Mar. 4, 2003, vol. 100, No. 5, p. 2558-2561.

* cited by examiner

Crossing scheme for *yellow* rescue:

screen for $y^+$ w progeny; map $y^+$

Crossing scheme for *yellow* disruption:

screen for $y$ $w^+$ male progeny; map $w^+$

ENDS-OUT GENE TARGETING METHOD

The present application claims the priority of U.S. Provisional Patent Application Ser. No. 60/416,561, that was filed on Oct. 7, 2002.

ACKNOWLEDGMENT OF FEDERAL RESEARCH SUPPORT

The U.S. Government has certain rights in the invention, based upon partial support by Grant No. R21GM57792 from the National Institutes of Health, U.S. Public Health Service.

FIELD OF INVENTION

The present invention relates to a gene targeting method for use in a variety of animals and plants, including insects (most preferably *Drosophila*), and mammals, whereby ends-out, or replacement, gene targeting occurs. Additionally, the present invention relates to a construct that can be used in targeting specific genes in a selected host organism and the resultant transfected host organism.

BACKGROUND OF INVENTION

When exogenous DNA, RNA or a nucleic acid molecule is introduced into a cell, the cell is said to be transfected, known previously as transformed. Various methods are known by which the transfecting nucleic acid molecule becomes a permanent part of the transformed cell's genome. Unless specialized methods are used, permanent transformation is usually the result of integration of the transforming nucleic acid into chromosomal DNA at a random location. The transfecting DNA, or nucleic acid molecule, can also be introduced into the cell on a plasmid that replicates autonomously within the cell and which segregates copies to daughter cells when the cell divides. Either way, the locus of the transfecting nucleic acid molecule, with respect to endogenous genes of the cell, is unspecified. Gene targeting is the general name for a process, whereby chromosomal integration of the transfecting DNA, at a desired genetic locus, is facilitated to the extent that permanently transfected cells having the DNA at that locus can be obtained at a useful frequency. Typically, the gene at the target locus is modified, replaced, or duplicated by the transforming or transfecting (donor) nucleic acid molecule. As such, it is desired to have a method for targeting specific genes in animals, such as non-human mammals, amphibians, and insects, especially *Drosophila*, since it is a well-known model organism.

Generally, the steps taken to achieve gene targeting are intended to increase the likelihood of chromosomal integration at the desired locus and to select for the desired integration events that have occurred (or select against undesired integration events). Without such steps, the desired integration might occur by chance, but with such a low frequency as to be undetectable.

Yeast (*Saccharomyces cerevisiae*) has been a useful organism for the development of gene targeting methods. Rothenstein, R. (1991) *Methods in Enzymology* 194:281-301, reviewed techniques of targeted integration in yeast. The normal yeast process of homologous recombination was shown to permit integration of transforming plasmid DNA having a segment of sequence homologous to a selected yeast gene. When a double-strand break was introduced within the homologous segment, transformation with the resulting linear DNA resulted in a 10-1000-fold increased incidence of integration at or near the break. The longer the region of homology on either side of the break, the greater the frequency of recombination at the desired locus. Strategies for gene replacement, gene disruption, and rescue of mutant alleles were described in the above article.

The studies of gene targeting in yeast have been facilitated by the fact that individual transformed cells can be isolated and grown in pure culture to any convenient amount. In addition, the short doubling time of yeast cells in culture has allowed researchers to observe events that occur with a low frequency and to study the genetics of those events within a convenient time scale. When working with complex multicellular organisms, the number of individuals which can be assessed for a genetic change, and the time scale required for observing patterns of inheritance, are both increased. To achieve practical gene targeting in such organisms, techniques were developed to increase the frequency of observable targeting events and to increase the efficiency of selection for desired events. Practical methods of gene targeting have been developed in the fruit fly, *Drosophila melanogaster*, and in the mouse, *Mus musculus*, however, such methods have not been applicable to a wider range of organisms. One of the methods for gene targeting in *Drosophila* relates to an ends-in procedure.

Transposons have been utilized for inducing gene targeting in *Drosophila*. A transposon is a class of nucleic acid sequence that can move from one chromosomal site to another. Gloor, G. B., et al. (1991) *Science,* 253:1110-1117, described utilizing the property of the P element transposon to generate a double strand gap when a transposition event occurs, the gap being located at the site formerly occupied by the transposon. Under most circumstances, the resulting gap is repaired by copying from homologous sequences on the sister chromatic. If a homologous sequence is present in the cell at an ectopic locus, for example on a plasmid, that sequence can also serve as a template to repair the double strand gap generated by the transposon's departure. This type of gap repair can then be employed to target a desired sequence to the locus of the departing transposon. The primary limitation of the process is that the host organism must have a transposon located at or near the target site.

The FLP-FRT recombinase system of yeast was employed to mobilize FRT-flanked donor DNA and generate re-integration at a different chromosomal location (Golic, M. M., et al., (1997) *Nucl. Acids Res.* 25:3665-3671). The donor DNA was introduced into the *Drosophila* chromosome flanked by repeats of the FRT recombinase recognition site, all within a P element for integration. The FLP recombinase was introduced under control of a heat-shock promoter, so that the enzyme could be activated by the investigators at a specified time. The action of FLP recombinase resulted in excision of the donor DNA followed by a second round of recombination at a target site where another FRT site was present. The phenomenon could be observed by using flies having the target FRT site at the locus of a known gene where an altered phenotype was detectable. This method is limited by the requirement of a target FRT site near a known gene.

Gene targeting in mammals has only been achieved, to any significant degree, in the mouse. Uniquely, in the case of the mouse, a pluripotent cell line exists, whereby embryonic stem (ES) cells can be grown in culture, transformed, selected, and introduced into an embryonic stage, preferably the blastocyst stage of the mouse embryo. Embryos bearing inserted transgenic ES cells develop as genetically chimeric (individuals composed of genetically different cells) offspring. By interbreeding siblings, homozygous mice carrying the selected genes can be obtained. An overview of the process and its limitations is provided by Capecchi, M. R. (1989) *Trends in Genetics* 5:70-76; and by Bronson, S. K. (1994) *J. Biol. Chem.* 269:27155-25158.

Both homologous and non-homologous recombination occurs in mammalian cells. Recombination is the occurrence of progeny with combinations of genes other than those that occurred in the parents, due to independent assortment or crossing over. Both homologous and non-homologous processes occur with low frequency and non-homologous recombination occurs more frequently than homologous recombination. ES cells are transfected with a DNA construct that combines a donor DNA having the modification to be introduced at the target gene site, with a flanking sequence homologous to the target site, and marker genes, as needed, for selection, as well as any other sequences that may be desired. The donor construct need not be integrated into the chromosome initially, but can recombine with the target site by homologous recombination, or at a non-target site by non-homologous recombination. Since these events are rare, dual selection is required to select for recombinants and to select against non-homologous recombinants. The selections are carried out in vitro on the ES cells in culture. PCR screening can also be employed to identify desired recombinants. The frequency of homologous recombination is increased as the length of the region of homology in the donor is increased, with at least 5 kb of homology being preferred. However, homologous recombination has been observed with as little as 25-50 bp of homology. Donor DNA, having small deletions or insertions of the target sequence, are introduced into the target with higher frequency than point mutations. Both insertions of sequence and replacement of the target, as well as duplication in whole or in part of the target, can be accomplished by appropriate design of the donor vector and the selection system, as desired, for the purpose of the targeting.

Gene targeting in mammals, other than the mouse, has been limited by a lack of ES cells capable of being transplanted and of contributing to germline cells of developing embryos. However, techniques related to cloning technology have opened new possibilities for gene targeting in other species. McCreath, K. J., et al. (2000) *Nature* 405:1066-1069, have reported successful targeting in sheep by carrying out transformation and targeting selection in primary embryo fibroblast cells. Fibroblast nuclei that were successfully targeted were then transferred to enunciated egg cells, followed by implantation in the uterus of a host mother. The technique provides the advantage that the generation of chimeric animals and subsequent breeding to homozygosity are not required. However, the time available for carrying out targeting and selection is comparatively short.

The use of recombinases and their recognition sites has proven to be a valuable tool once the initial targeting event has been achieved. For a review of the techniques applying the site-specific recombinase systems, see Sauer, B. et al. (1994), *Current Opinion in Biotech.* 5:521-527. See also U.S. Pat. No. 4,959,317. For example, repeated targeting at a given locus is facilitated by including recombination-specific recombination sites in the initial targeting construct. Once in place, the recombination sites can be used, in combination with the respective recombinases, to provide highly efficient transfer of an exogenous DNA to the locus of the recombination site. A recombinase system commonly used is the Cre recombinase, which recognizes a sequence designated loxP. The Cre recombinase and loxP recognition site are derived from bacteriophage P1.

Another widely used system, derived from the 2μ circle of *Saccharomyces cerevisiae*, is the FLP recombinase, which recognizes a specific sequence, FRT. In both systems, the effect of recombinase activity is determined by the orientation of the recognition sites flanking a given segment of DNA. A DNA sequence, flanked by directly repeated recombination sites and then integrated into the genome by either homologous or illegitimate recombination, can subsequently be removed simply by providing the corresponding recombinase. One useful consequence of this property has been exploited to remove an unwanted selection marker from the target site once homologous recombination has occurred and selection is no longer necessary. In another application, a gene which may exert a toxic effect can be maintained in a dormant state by inserting a lox-flanked sequence between the promoter and the gene, the sequence being designed to prevent expression of the gene. Expression of Cre activity results in excision of the intervening sequence and allows the promoter to act to activate the dormant gene. Cre can be introduced by mating or provided in an inducible form that permits activation at the investigator's control. A variety of other post-targeting strategies can be facilitated by the use of site-specific recombination systems, as known in the art.

As has been shown in yeast, introducing a double strand (ds) break into DNA increases recombination frequency. A number of studies have demonstrated that introducing a ds break into a target site increased recombination with a homologous donor DNA about 100-fold. The ds break was created by providing an I-SceI site in the target DNA, then introducing and expressing an I-SceI endonuclease, along with a donor DNA, homologous to the target. Using Chinese hamster ovary (CHO) cells, Sargent, R. G., et al. (1997) *Mol. Cell. Biol.* 17:267-277, described an experiment for testing crossovers between tandem repeats of an APRT gene, one of which carried an I-SceI site. The occurrence of homologous recombination could be measured by crossovers between the tandem APRT loci, which eliminated an intervening thymidine kinase (TK$^+$) gene, or within different segments of the APRT gene, itself, based on the presence or absence in the progeny of certain mutations located in one of the tandem genes. A ds break was generated at the I-SceI site by introducing and expressing the I-SceI endonuclease carried on a separate expression vector and introduced by transformation. A similar type of demonstration was reported by Liang, F., et al. (1998) *Proc. Natl. Acad. Sci. USA* 95:5172-5177. Cohen-Tannoudji, M. et al. (1998) *Mol. Cell. Biol.* 18:1444-1448, described the use of an I-SceI site introduced into a target gene by conventional targeting. Once in place, other constructs could be introduced at the same target ("knocked in") by a subsequent trans formation with a desired donor construct and transient expression of I-SceI endonuclease to introduce a ds-break at the target. The efficiency of the second targeting step was reportedly 100-fold greater than was observed for conventional targeting. The method had the disadvantage that an I-SceI site was required at the target site.

U.S. Pat. No. 5,962,327 describes the I-SceI endonuclease and its recognition site. The patent also discloses general strategies using I-SceI that can be attempted for the site-specific insertion of a DNA fragment from a plasmid into a chromosome. A diagram of site-directed homologous recombination in yeast is presented. It should be noted that this technique was shown only in yeast.

The difficulty of introducing a linear DNA molecule into germline cells hindered development of targeting techniques in *Drosophila*. Recently, a method to generate such a linear fragment in vivo was reported, accompanied by a demonstration of gene targeting (Rong and Golic, 2000). The particular form of gene targeting that was shown is termed ends-in or insertional targeting. This occurs when a DNA double-strand break (DSB) is made within a stretch of DNA that provides contiguous homology to the target locus, and results in the insertion of the extrachromosomal donor to generate a duplication of the targeted region. An alternative arrangement, where DSBs are provided at each end of a homologous segment, is termed ends-out targeting, and causes a segment of chromosome to be replaced with an introduced segment (FIG. 1). In mouse and in yeast, some studies show that ends-out targeting is less efficient than ends-in, while others indicate that the two types can be equally efficient (Hastings et al., 1993, Hasty et al., 1991, Thomas et al., 1987, and Deng et al., 1992). Although ends-out targeting has been successful and extremely useful in other model eucaryotes, doubts about its efficacy in *Drosophila* have been raised because of a previous failure to obtain targeting by this method (Bellaiche et al., 1999).

Ends-in and ends-out targeting refer to the two arrangements of donor DNA that can be used for gene targeting. Both methods have been used for targeted mutagenesis, but require different designs of the DNA used for targeting. Ends-in targeting has been successful in *Drosophila*, but an earlier attempt at ends-out targeting had failed. Ends-in and Ends-out targeting methods and constructs are readily distinguished. In particular, an ends-in construct has only one DSB site. In certain instances, the efficiency with which ends-in promotes targeting is inadequate. Additionally, ends-in is not well suited for use as a rescue construct.

In a previous attempt at ends-out targeting in *Drosophila*, Bellaiche et al. (1999) failed to recover gene targeting events when screening for ends-out disruption of the white gene. A consideration of that failure may provide useful insight into constraints on the use of gene targeting in *Drosophila*. Bellaiche and colleagues chose to drive FLP and I-SceI expression with the B2-tubulin promoter, a male germline-specific promoter that drives transcription in primary spermatocytes. When targeting events were recovered from males, the events may have occurred in mitotic, not meiotic cells, because the heat shock promoter that was used was limited in its activity to the earliest stages of spermatogenesis (Bonner et al., 1984; Golic and Golic, 1996). Meiotic cells of the male germline, in which meiotic recombination does not occur, may be even less favorable to targeting. Furthermore, although the B2-tubulin promoter drives transcription pre-meiotically, it was found that, with a B2-tubulin-promoted FLP gene that was constructed, translation of the mRNA was predominantly post-meiotic (Golic et al., 1997). If the same was true for the constructs made by Bellaiche et al., then the attempted targeting may have occurred primarily in post-meiotic spermatic.

A second difference is that a large non-homologous stretch of DNA was located on one end of the homologous segment. It is conceivable that this interfered with targeting. In mouse ES cell targeting, however, this does not pose a significant impediment to targeting efficiency, thus, the preferred explanation is that B2-tubulin-promoted expression of the recombinase and endonuclease for the failure to obtain targeting is favored.

As such, it is desired to have additional gene targeting methods for use in *Drosophila*. It is especially desired to have an ends-out method that will work in *Drosophila*.

SUMMARY OF INVENTION

The present invention includes methods and compositions for carrying out gene targeting, in particular, ends-out targeted recombination in *Drosophila*. Unlike previously known methods for gene targeting in multicellular organisms, the present invention does not depend on the availability of a pluripotential cell line and, hence, can be adapted for gene targeting in any organism. The method exploits homologous recombination processes that are endogenous in the cells of all organisms. Any gene of an organism can be modified by the method of the invention, as long as the sequence of the gene, or a portion of the gene, is known, or in cases where a DNA clone is available.

"Target" is the term used herein to identify the genetic element or DNA segment to be modified. "Donor" is used herein to identify those genetic elements or DNA segments used to modify the target. The modification can be any sort of genetic change, including substitution of one segment for another, insertion of single or multiple nucleotide replacements, deletion, insertion, duplication of all or part of the target, and combinations thereof. Preferably, the modification is a substitution or replacement.

In general outline, a donor construct is provided within cells of the organism. The donor construct can be integrated anywhere in the genome, without regard to the locus of the target. Alternatively, the donor construct can be carried on an autonomously replicating genetic element, or present transiently. The donor construct includes a version of the target, the target modifying sequence containing any sequence modifications to be introduced at the target site, or can be a non-mutant donor to correct the mutant form. The construct includes two unique endonuclease sites and two recombinase recognition sites. After recombination, a unique endonuclease able to recognize the sites is introduced to cause two double strand breaks, generating a linear recombinogenic donor. The combination of the excision and endonuclease cutting, frees the recombinogenic donor to undergo homologous recombination at the target site, resulting in the desired genetic change at the target. If the donor construct is not chromosomally integrated, but merely present on a plasmid in the host cell, the excision step is not needed. As described herein, the use of various selectable markers at specified positions of the donor construct relative to the modifying sequence, facilitates identifying recombinants and selecting for the desired type of recombinant.

The timing of the excision and endonuclease steps is controlled by maintaining the enzymes that catalyze these reactions under inducible or tissue-specific expression control. The genes encoding the enzymes, combined with their promoters or mRNA encoding the enzymes, or the enzymes themselves, can be introduced to the organism concomitantly with the donor construct. Alternatively, a transgenic strain of the organism carrying the genes can be provided by a prior step of transformation and selection. Such a strain is termed herein a carrier host organism. A carrier host organism is useful as a host for all desired target gene modifications of the host species.

Many alterations and variations of the invention exist as described herein. The invention is exemplified for gene targeting in the insect, *Drosophila*. Increasingly larger segments of genomic sequences are becoming known for a growing number of organisms. The functional elements used to carry out the steps of the invention are known for any desired organism. Therefore, the present invention can be adapted for application in any organism. The invention, therefore, provides a general method for gene targeting in any organism, as well as a method for making a carrier host strain of any organism. Products of the invention include transformation vectors for gene targeting that include a modifying sequence having two unique endonuclease recognition sites associated therewith, such that endonuclease cutting at the sites yields a recombinogenic donor. The invention also provides a transformation vector for generating a carrier host organism, including an endonuclease capable of making a double strand break in DNA at the unique site, the endonuclease being under control of an inducible promoter.

The present invention relates to a method of gene targeting for use in a transformable host organism. The method is initiated by choosing a target gene of the host organism or portion thereof having a known or cloned sequence. An ends-out donor construct is formed by flanking the donor target with a pair of unique endonuclease sites. A pair of recombinase recognition sites flank the unique endonuclease sites. The host organism is then transfected with the donor construct. Once the host organism is transfected, endonuclease and recombinase enzymes directed to the endonuclease and recombination sites must be made available in the host. This can be done by expressing transgenes in the host to produce a recombinogenic donor. A linear fragment containing the segment homologous to the target gene is ultimately produced. Finally, progeny of the host organism in which recombination between the target and the recombinogenic donor has occurred are selected.

The invention further relates to a transformation vector for ends-out targeting. The vector is formed from a target gene modifying sequence that is homologous with a specified target gene or portion thereof, two unique endonuclease sites which flank the modifying sequence, and two recombination sites which flank the endonuclease sites.

The invention also relates to a transfected host organism. The organism is transfected with the above transformation vector.

The present invention is advantageous because a method for practicing ends-out gene targeting is provided. In particular, a method for targeting in insects is provided.

DETAILED DESCRIPTION OF INVENTION

Figure 1:
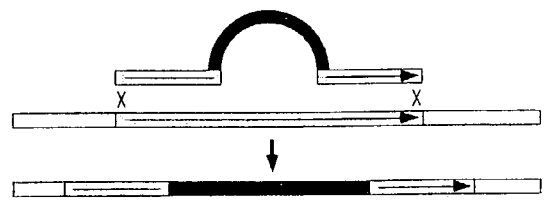
FIG. 1 shows two general forms of gene targeting, with donor DNA molecules diagramed above their targets, along with the expected products of recombination.
Figure 1:
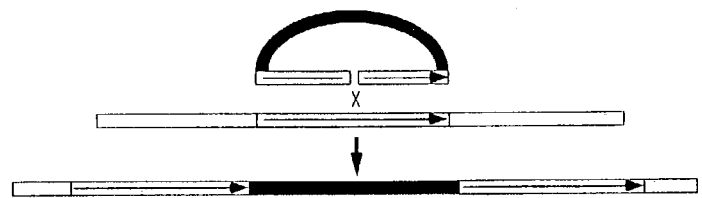

The present invention relates to methods and constructs for use in gene targeting. In particular, the present invention relates to an ends-out gene targeting method and the related construct. In contrast to previously known methods for gene targeting in multicellular organisms, the present invention does not depend on availability of a pluripotential cell line, and is adaptable to any organism. The method, however, is especially well suited for use in insects, especially *Drosophila*. Any gene or nucleic acid molecule of an organism can be modified by the method, as the method exploits homologous recombination processes that are endogenous in the cells of all organisms.

The method relates to formation of a donor construct which includes the target gene or targeted nucleic acid molecule, two rare endonuclease cut sites, and two recombinogenic sites. In the alternative, one rare endonuclease cut site may be used. The target nucleic acid sequence will be flanked first by the endonuclease cut sites, with the endonuclease cut sites flanked by the recombinogenic sites. The construct is preferably placed in a P element transposon; however, other means for inserting the construct into a host may be used. Other available transposons include Mariner and Sleeping Beauty. The target construct is well suited for use in insects, especially *Drosophila*, and can be used to rescue or disrupt a gene.

The following terms are used herein according to the following definitions:

"Gene targeting" is a general term for a process wherein homologous recombination occurs between DNA sequences residing in the chromosome of a host cell, or host organism, and a newly introduced DNA sequence.

"Host organism" is the term used for the organism in which gene targeting, according to the invention, is carried out.

"Target" refers to the gene or DNA segment or nucleic acid molecule, subject to modification by the gene targeting method of the present invention. Normally, the target is an endogenous gene, coding segment, control region, intron, exon, or portion thereof, of the host organism. The target can be any part or parts of genomic DNA.

"Target gene modifying sequence" is a DNA segment having sequence homology to the target, but differing from the target in certain ways, in particular, with respect to the specific desired modification(s) to be introduced in the target.

"Unique endonuclease site" is a recognition site or sites for an endonuclease that catalyzes a double strand break in DNA at the recognition site. Any recognition site that does not otherwise exist in the host organism, or does not exist at a site where double strand breakage is harmful to the host organism, can serve as a unique endonuclease site for that organism. "Unique" is, therefore, an operational term. Furthermore, modified host organisms may be generated in which an endogenous site or sites have been modified, so that they are no longer recognized by the endogenous endonuclease. Such a modified host organism can be generated by expressing the endonuclease in the organism and selecting for individuals that are resistant to harmful effects of such expression. Such resistant individuals can arise by cutting, followed by inaccurate repair of the break and consequent alteration of the recognition sequence. Alternatively, within a population of individuals, pre-existing polymorphisms may already exist and be selected for by expression of the endonuclease. Many classes of enzymes catalyze double strand DNA breakage in a site-specific manner, identified by a specific nucleotide sequence at or near the break point. Such enzymes include, but are not limited to, transposases, recombinases, and homing endonucleases. By introducing the nucleotide sequence of a unique endonuclease site into a donor construct, a double strand break can be generated at or near that site by action of the appropriate endonuclease. A preferred class of unique endonuclease sites of practical utility are the homing endonuclease or rare-cutting endonuclease sites. The rare-cutting endonuclease sites are typically much longer than restriction endonuclease sites, usually ten or more base pairs in length and, thus, occur rarely, if at all, in a given host organism. For a review of the rare-cutting endonucleases and details of their recognition site sequences, see Belfort, M. et al., (1997) *Nucl. Acids Res.* 25:3379-3388, incorporated herein by reference. Some of the rare-cutting endonucleases are encoded by organelle genomes, and the coding sequences may use non-standard coding. The coding sequences of many such endonucleases are known and have, or can be, modified to be expressible from a chromosomal locus. The expression can be controlled, if desired, by an inducible promoter. In principle, any rare-cutting endonuclease can be employed in the practice of the invention, including, for example, I-CreI, I-SceI, I-TIi, I-CeuI, I-PpoI, and PI-PspI. Presently, I-SceI is the most preferred endonuclease.

"Marker" is the term used herein to denote a gene or sequence whose presence or absence conveys a detectable phenotype of the organism. Various types of markers include, but are not limited to, selection markers, screening markers, and molecular markers. Selection markers are usually genes that can be expressed to convey a phenotype that makes the organism resistant or susceptible to a specific set of conditions. Screening markers convey a phenotype that is a readily observable and a distinguishable trait. Molecular markers are sequence features that can be uniquely identified by oligonucleotide probing, for example, RFLP (restriction fragment length polymorphism), SSR markers (simple sequence repeat), and the like.

"Donor construct" is the term used herein to refer to the entire set of DNA segments to be introduced into the host organism as a functional group, including at least the modifying sequence(s), two or more unique endonuclease sites, and two or more recombinase target sites, as well as other DNA segments as desired and, optionally, one or more markers. In one embodiment of the invention, the donor construct is flanked by transposon target sites so that the donor construct becomes integrated somewhere in the host genome after being introduced into host cells. Preferably, the donor construct is inserted into a transposable element. An excisable donor construct is one which can be excised (freed) from its location on the host chromosome, or on an extrachromosomal plasmid, by the action of an inducible enzyme, for example, a unique restriction enzyme, or a recombinase. In order to be excisable, the donor construct must be flanked by recognition sites for the excising enzyme. For example, in the upper diagram of FIG. 2, the donor construct is flanked by FRT sites, which render the construct excisable by the FLP recombinase.

"Recombinogenic donor" is the term used herein to describe the structure of that part of the donor construct resulting from the action of the unique endonuclease and the recombinase. The recombinogenic donor is not integrated into the host chromosome and is characterized by having a segment homologous to the target flanked by broken ends in the case of ends-out targeting. For example, a recombinogenic donor, resulting from the action of a recombinase and a unique endonuclease acting on the recognition sites flanking a target gene modifying sequence, could have a structure, whereby a linear DNA with endonuclease-cut ends is formed. The donor construct is designed for ends-out targeting, and results in replacement of a segment of the target, as shown in FIG. 1.

"Recombinase" is the term known in the art for a class of enzymes which catalyze site-specific excision and integration into and out of a host chromosome or a plasmid. At least 105 such enzymes are known and reviewed generally, with references, by Nunes-Duby, S. et al. (1998) *Nucleic Acids Res.* 26:391-406, incorporated herein by reference. It is anticipated that novel recombinases will be discovered and can be utilized in the invention. Two well-known and widely used recombinases are FLP, isolated from yeast, and Cre, from bacteriophage P1. Both enzymes have been shown to be expressible and functional in both procaryotes and eucaryotes. Site specificity of a recombinase is provided by a specific recognition sequence, which is termed a recombinase target sequence herein. The recombinase target sequences for FLP and Cre are designated FRT and lox, respectively.

The control of gene expression is accomplished by a variety of means well-known in the art. Expression of a transgene can be constitutive or regulated to be inducible, or repressible by known means, typically by choosing a promoter that is responsive to a given set of conditions, for example, presence of a given compound, or a specified substance, or change in an environmental condition, such as temperature. In examples described herein, heat shock promoters were employed. Genes under heat shock promoter control are expressed in response to exposure of the organism to an elevated temperature for a period of time. The term "inducible expression" extends to any means for causing gene expression to take place under defined conditions, the choice of means and conditions being chosen on the basis of convenience and appropriateness for the host organism.

A "carrier host organism" is one that has been stably transformed to carry one or more genes for expression of a function used in the process of the invention. Functions which can be provided in a carrier host organism include, but are not limited to, unique restriction endonucleases and recombinases.

Many of the genetic constructs used herein are described in terms of the relative positions of the various genetic elements to each other. "Adjacent" is used to indicate that two genetic elements are next to one another without employing actual fusion of the two sequences. For example, two segments of DNA adjacent to one another can be separated by oligonucleotides providing a restriction site, or having no apparent function. "Flanking" is used to indicate that the same, similar, or related sequences exist on either side of a given sequence. For example, in the upper diagram of FIG. 2, the $y^+$ gene is shown flanked by I-SceI site segments. That construct is, in turn, flanked by FRT sites oriented parallel to one another. Segments described as "flanking" are not necessarily directly fused to the segment they flank, as there can be intervening, non-specified DNA. These and other terms used to describe relative positions are used according to normal accepted usage in the field of genetics.

The method of the invention can be used for gene targeting in any organism. Minimum requirements include a method to introduce genetic material into the organism (either stable or transient transformation), existence of a unique endonuclease that can be expressed in the host organism (or a modified host organism) without harming the organism, and sequence information regarding the target gene or a DNA clone thereof. It is also necessary to have the recombinase expressed in the host organism. The efficiency with which homologous recombination occurs in the cells of a given host varies from one class of organisms to another. However, the use of an efficient selection method or a sensitive screening method can compensate for a low rate of homologous recombination. Therefore, the basic tools for practicing the invention are available to those of ordinary skill in the art for such a wide range and diversity of organisms that the successful application of such tools to any given host organism is readily predictable.

Transformation can be carried out by a variety of known techniques, depending on the organism, or characteristics of the organism's cells, and of its biology. Stable transformation involves DNA entry into cells and into the cell nucleus. For single-celled organisms and organisms that can be regenerated from single cells (which includes all plants and some mammals), transformation can be carried out by in vitro culture, followed by selection for transformants and regeneration of the transformants. Methods often used for transferring DNA or RNA into cells include micro-injection, particle gun bombardment, forming DNA or RNA complexes with cationic lipids, liposomes, or other carrier materials, electroporation, and incorporating transforming DNA or RNA into virus vectors. Other techniques are known in the art and may also be used. For a review of the state of the art of transformation, see standard reference works such as Methods in Enzymology, Methods in Cell Biology, Molecular Biology Techniques, all published by Academic Press, Inc., N.Y. It is most preferred, however, to use a virus vector. DNA transfer into the cell nucleus occurs by cellular processes, and can sometimes be aided by choice of an appropriate vector by including integration site sequences, which can be acted upon by an intracellular transposase or recombinase. For reviews of transposase or recombinase mediated integration see, e.g., Craig, N.LK. (1988) *Ann. Rev. Genet.* 22:77; Cox, M. M., FLP site-specific recombination system of *Saccharomyces cerevisiae* (1988) In *Genetic Recombination* (R. Kucherlapati and G. R. Smith, eds.) 429-443, American Society for Microbiology, Washington, D.C.; Hoess, R. H. et al. (1990) In *Nucleic Acid and Molecular Biology* (F. Eckstein and D. M. J. Lilley eds.) Vol. 4, 99-109, Springer-Verlag, Berlin. Direct transformation of multicellular organisms can often be accomplished at an embryonic stage of the organism. For example, in *Drosophila*, as well as other insects, DNA can be micro-injected into the embryo at a multinucleate state where it can become integrated into many nuclei, some of which become the nuclei of germline cells. By incorporating a marker as a component of the transforming DNA, non-chimeric progeny insects of the original transformant individual can be identified and maintained. Direct microinjection of DNA into egg or embryo cells has also been employed effectively for transforming many species. In the mouse, the existence of pluripotent embryonic stem (ES) cells that are culturable in vitro has been exploited to generate transformed mice. The ES cells can be transformed in culture, then micro-injected into mouse blastocysts, where they integrate into the developing embryo and, ultimately, generate germline chimeras. By interbreeding heterozygous siblings, homozygous animals carrying the desired gene can be obtained. Recently, stable germline transformations were reported in mosquito (Catteruccia F., et al. (2000) *Nature* 405:954-962). For reviews of the methods for transforming multicellular organisms, see, e.g., Haren, et al. (1999) *Annu. Rev. Microbiol.* 53:245-281; Reznifoff, et al. (1999) *Biochem. Biophys. Res. Commun.* December 29:266(3);729-734; Ivics, et al. (1999) 60:99-131; Weinberg (1998) March 26:8(7):R244-247; HALLET, BERNARD et al. (1997) *FEMS Microbiol. Rev.* Vol. 21, p. 157-178; Craig (1997) *Annu. Rev. Biochem.* 66:437-474; Beall, et al. (1997) *Genes Dev.* August 15:11 (16):2137-2151.

A unique endonuclease site can be a recognition site for a rare-cutting endonuclease or for any other enzyme that generates a double stranded break in DNA at the recognition sites, including, for example, a transposase. The only requirement for the invention is that the enzyme does not act elsewhere on the genome of the organism, or at a minimum, that activity of the enzyme does not reduce viability of the organism significantly.

Markers are used for a variety of purposes known in the art of genetics. A molecular marker, such as an RFLP or SSR marker can serve to indicate the presence of a given gene or DNA sequence linked to it, and can also provide location information relative to the presence of other markers. A selectable marker is a segment of genetic information, usually a gene which, when expressed, can convey a reproductive differential or survival advantage or disadvantage to the organism possessing the marker, under environmental conditions, which the investigator can control. Positive selection is provided when the marker conveys an advantage to the organism or cell possessing it, compared to those lacking it. Negative selection is provided when the marker conveys a relative disadvantage to an organism or cell possessing the marker. A selectable marker gene can be constitutive or placed under inducible expression control, so that the selection can be activated or inactivated under the control of the investigator. Positive selection can be provided, for example, by a gene conferring resistance to an antibiotic or other toxin so that in the presence of the toxin cells lacking the resistance are less viable than cells possessing the resistance. Similarly, negative selection is provided by a gene conferring sensitivity to a specific compound, so that cells possessing the gene are selectively killed in the presence of the toxin. The foregoing are merely examples of the great variety and complexity of markers used for selection, and of selection systems, in general, which are known in the art, and fundamental to the practice of genetics. Markers for screening are those which convey an identifiable trait (phenotype) to cells or organisms possessing the marker, which trait is lacking in cells or organisms that do not possess the marker. An antigen not normally present in the organism or in individual cells can serve as a screening marker, using a fluorescent-tagged antibody or other tag to identify the antigen's presence. Many screening markers are known and available to those skilled in the art. The use of markers is exemplified for various aspects of the invention; however, it will be understood that the manner of using markers, and the choice of a particular marker type in a given situation, is well understood in the art, and that the invention does not depend on the use of any particular type of marker.

"Recombination," in the context of the present invention, is a term for a process in which genetic material, at a given locus, is modified as a consequence of an interaction with other genetic material. "Homologous recombination" is recombination occurring as a consequence of interaction between segments of genetic material that are homologous, or identical, at least over a substantial length of nucleotide sequence. The minimal necessary length is functionally defined and may vary from cell to cell, or organism to organism (i.e., between species). Homologous recombination is an enzyme-catalyzed process that occurs in essentially all cell types. The reaction takes place when nucleotide strands of homologous sequence are aligned in proximity to one another, and entails breaking phosphodiester bonds in the nucleotide strands and rejoining with neighboring homologous strands, or with an homologous sequence on the same strand. The breaking (cutting) and rejoining (splicing) can occur with precision, such that sequence fidelity is retained. Homologous recombination between a target gene and a donor construct of identical sequence, except for a marker, can result in reconstitution of the target, distinguishable only by the presence of the marker. Homologous recombination occurs only rarely, if ever, unless the donor and the target can be present in physical proximity to one another.

In one embodiment of the invention, the donor construct is integrated at a chromosomal site that is not near the target. The cells are then provided with means for freeing the recombinogenic donor from its chromosomal locus to allow homologous recombination to take place. In particular, recombinase is used to extract the donor construct from the chromosomal locus followed by cutting with the unique endonuclease to form a linear fragment, which contains the target gene modifying sequence. In another embodiment, the donor construct is present in the cell but not integrated into the chromosome, for example, as an autonomously replicating plasmid or as a non-replicating, transiently present plasmid. In either case, the donor construct is free to approach the target, and the action of rendering the donor recombinogenic by introducing a double strand DNA break, stimulates homologous recombination with the target.

The frequency of homologous recombination is influenced by a number of factors. Different organisms vary with respect to the amount of homologous recombination that occurs within the organism's cells, and the relative proportion of homologous to non-homologous recombination that occurs is also species-variable. The length of the donor-target region of homology affects the frequency of homologous recombination events, the longer the region of homology, the greater the frequency. The length of the homology region needed to observe homologous recombination is also species-variable. However, differences in the frequency of homologous recombination events can be offset by the sensitivity of selection for the recombinations that do occur. With sufficiently sensitive selection, e.g., by choosing a combination of positive and negative selection, virtually every recombination event can be identified. Other factors, such as the degree of homology between the donor and the target sequences will also influence the frequency of homologous recombination events, as is well understood in the art. It will be appreciated that absolute limits for the length of the donor-target homology, or for the degree of donor-target homology, cannot be fixed, but depend on the number of potential events which can be scored, and the sequence of selection. Where it is possible to screen $10^9$ events, for example, in cultured cells, a selection that can identify 1 recombination in $10^9$ cells will yield useful results. Where the organism is larger, or has a longer generation time, such that only 100 individuals can be scored in a single test, the recombination frequency must be higher and selection sensitivity is less critical. All such factors are well known in the art, and can be taken into account when adapting the invention for gene targeting in a given organism. The invention can be most readily carried out in the case of organisms which have rapid generation times, or for which sensitive selection systems are available, or for organisms that are single-celled, or for which pluripotent cell lines exist that can be grown in culture and which can be regenerated or incorporated into adult organisms. In the former case, the invention is demonstrated for the fruit fly, *Drosophila*. It will be understood by those skilled in the art that the invention is operative, independent of the method used to transform the organism. Further, the invention is readily applied to such disparate organisms, as plants and insects, with widespread applicability of the invention to living organisms.

The organisms in which gene targeting can be accomplished according to the invention include, but are not limited to, insects, including insect species of the orders *Coleoptera, Diptera, Hemiptera, Homoptera, Hymenoptera, Lepidoptera*, and *Orthoptera*; plants, including both monocotyledonous plants (monocots), including, but not limited to, maize, rice, wheat, oats, and other grain crops, and dicotyledonous plants (dicots), including, but not limited to, potato, soybean, and other legumes, tomato, members of the *Brassica* family, *Arabidopsis*, tobacco, grape, and ornamental species, such as roses, carnations, orchids, and the like; mammals, including known transformable species, such as mouse, rat, sheep, and pig, and others, as transformation methods are developed, including bovine and primates, including humans; birds, including food species, such as chicken, turkey, duck, and goose; fish, including species raised for food or sport, including trout, salmon, catfish, tilapia, ornamental breeds, such as koi and goldfish, and the like; and shellfish, including oyster, clam, shrimp, and the like. Gene targeting in such organisms is useful to accomplish genetic modification to impart disease resistance, improve hardiness and vigor, remove genetic defects, improve product quality or yield, impart new desirable traits, alter growth rates or, in the case of pest species and disease vectors, introduce, alter, or remove genes affecting the ability if the pest or vector to spread disease or cause damage. The present method is especially useful for determining what phenotypic causes result from certain genes.

It will be understood that the invention is also useful for gene targeting in somatic cells and tissues, and is not limited to germline or pluripotent cells. Targeting in somatic cells provides the ability to make desired and specific genetic modification to target host cells and tissues. Targeting in somatic cells now provides a means of producing transgenic animals through the nuclear transfer technique (McCreath, K. J. et al. (2000) *Nature,* 405:1066-1069; Polejaeva, I. A. et al. (2000) *Nature* 407:86-90). Transformation methods using tissue or cell-type-specific vectors can be employed for providing a desired donor construct in the cells of choice, or the cells can be transformed by non-specific means, using tissue-specific promoters to ensure activation of targeting the cells of choice. Obvious choices include tumor cells and specific tissues affected by a genetic defect. The methods of the invention are, therefore, useful to expand and supplement the available techniques of gene therapy.

A factor which influences targeting efficiency is the extent of homology or nonhomology between donor and target. There are many reports showing that increased donor:target homology increases the absolute targeting frequency in mammalian cells, see e.g., Shulman, M. J., et al. (1990) *Mol. Cell. Biol.* 10:466, Deng, C. and Capecchi, M. R. (1992) *Mol. Cell. Biol.* 12:3365. In *Drosophila*, investigators have examined the effect of homology in the context of P transposon break-induced gene conversion. The double strand break that is left behind when a P element transposes is a substrate for gene conversion, and may use ectopically-located homologous sequences as a template. Dray and Gloor found that as little as 3 kb of total template:target homology sufficed to copy a large non-homology segment of DNA into the target with reasonable efficiency. (Dray, T. and Gloor, H. G. B. (1997) *Genetics* 147:684, Scheeber, J. B. and Adair, G. M. (1994) *Mol. Cell. Biol.* 14:6663). In prior work on FLP-mediated DNA mobilization, very different efficiencies were observed for FLP-mediated integration at a target FRT when comparing experiments in which the donor and target shared different extents of homology (Golic, M. M. (1997) *Nucleic Acid Res.* 25:3665). Integration was approximately 10-fold more efficient when the donor and target shared 4.1 kb of homology than when they shared only 1.1 kb of homology, suggesting the possibility that interactions between an extrachromosomal DNA molecule and a chromosomal sequence may be stabilized to some degree by shared sequences. If the extent of homology is an important factor, increasing the extent of donor:target homology may increase the overall frequency of targeting and, as a consequence, provide a means to shift the ratio of targeted to non-targeted events. The limited data available from *Drosophila* leads us to conclude that 2-4 kb of donor:target homology is sufficient for efficient targeting. It is more preferred, however, if greater than 4 kb of donor:target homology is used.

The gene targeting technique of the invention is sufficiently efficient that chemical or genetic selection methods were unnecessary for the described embodiment, but these methods can be implemented as part of the scheme, if desired. Furthermore, the procedure, in general, does not require special lines of cultured cells, as does mouse gene targeting. Because the technique can be carried out in the intact organism, it can be used for gene targeting in many other species of animals and plants, with the only requirement being that a method of transformation exist.

It will be understood that for each of the specific features of the process of the invention, as just described, there exists a panoply of functional equivalents which can be employed, as desired and as appropriate, to carry out the invention.

Use of Other Site-specific Recombinases and Site-specific Endonucleases.

There are a large number of site-specific recombinases known that function similarly to FLP and that can be substituted in this procedure. For example, the Cre recombinase and its lox target site can be employed instead of the FLP-FRT system. Many other site-specific recombinases are listed by Nunes-Duby et al. (1998) *Nucleic Acids Research* 26:391-406, and there are no doubt many yet to be found. However, the FLP -FRT system is most preferred.

The I-SceI intron-homing endonuclease is also one of a large number of functionally similar rare-cutting endonucleases. Many of these, for instance, I-TliI, I-CeuI, I-CreI, I-PpoI, and PI-PspI, can be substituted for I-SceI in the targeting scheme. Many are listed by Belfort and Roberts (1997) *Nucleic Acids Research* 25:3379-3388). Many of these endonucleases derive from organelle genomes in which the codon usage differs from the standard nuclear codon usage. To use such genes for nuclear expression of their endonucleases, it may be necessary to alter the coding sequence to match that of nuclear genes. This can be done by synthesizing the gene as a series of oligonucleotides that are then ligated together in the proper order to produce a segment of DNA that encodes the entire endonuclease with nuclear codon usage.

Introduction of Mutations.

The gene targeting technique described herein can be used to substitute one allele for another at the targeted locus. This provides a way to insert large or small mutations into a targeted locus, or to convert a mutant allele into the wild-type allele. In cases where the mutant phenotype of the targeted gene is unknown, molecular techniques, such as PCR, can be used to detect the mutated allele.

Figure 2:
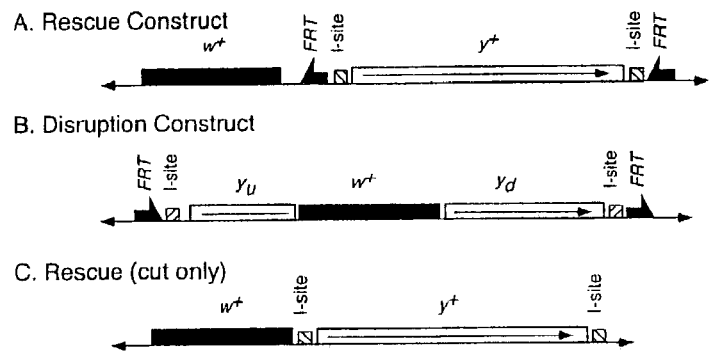
FIG. 2 is a diagram of the constructs for use in ends-out targeting, the locations of $y^+$ and $w^+$ genes are indicated, along with the FRTs and the I-SceI recognition sequences (I-site), $y_u$ and $y_d$ indicate the upstream and downstream portions of yellow, the small arrowheads at the left and right ends of each construct indicate the P element inverted repeat termini.

To make a donor construct, a transgenic vector DNA is engineered to carry a cloned copy (or partial copy) of the target gene with desired mutation or rescue construct, and one or two endonuclease cut sites, such as an I-SceI site. The cloned copy of the target gene is placed between two I-SceI recognition sites (FIG. 2). The donor version of the target is placed into a transposon vector between FRTs, along with an optional marker gene (such as the white$^+$ eye color gene) and transformed into a host, such as *Drosophila*.

In the second step, I-SecI endonuclease and FLP recombinase are introduced into the flies produced in step 1 (using a transgene or any of several other methods discussed herein). FLP-mediated recombination excises the donor from the chromosome. I-SecI-mediated cleavage at one or both of its target sites generates a linear DNA molecule that will recombine with a homologous chromosomal site.

Appropriate selection markers can be incorporated to identify stages of the process. Deletion of the target can, itself, serve as a selectable event, depending on the null phenotype. Other techniques of deletion targeting or replacement targeting can be employed, as known in the art for example, by employing an ends-out targeting construct.

Targeting by Use of a Site-specific Endonuclease Only.

Donor constructs can also be engineered to contain two unique endonuclease cut sites, such as I-SceI sites that flank a cloned donor version of the target locus and a marker gene. The cloned donor could be engineered in two halves so that the right half of the donor version of the target gene is located at the left end of the construct and vice-versa, with the marker gene between the halves. After introducing such a construct into the organism, double cutting at the flanking sites releases a donor molecule that is essentially identical to the released donor molecule shown in the lower half of FIG. 2.

Other ends-out targeting schemes are within the scope of the invention. Such schemes can involve the incorporation of a negatively selectable marker at a site, which can be used to favor targeted over non-targeted insertions, or at a site which can be used to eliminate progeny with the donor chromosome.

Use in Other Insects.

The method of the invention can be applied to other insects also. For a review of genetic manipulations in insects, see Insect Transgenesis Methods and Applications, Handler, A. M., and A. A. James eds. (2000) CRC Press, Boca Raton, Fla., which is incorporated by reference in its entirety. One potential problem in other insects is a paucity of genetic markers that can be followed to do the segregation screening. This paucity of markers applies to many other organisms in which the invention can be used for gene targeting. The problem can be dealt with by placing two dominant markers in the donor transgene. One of the markers (for instance, a green fluorescent protein [GFP] gene) would be placed outside the FRTs. The second marker (for instance, a chemical resistance gene) would be placed between the FRTs, along with the target locus. After freeing the donor construct, the first marker will stay in place, while the second marker will accompany the donor targeting DNA to the targeted locus. Therefore, after induction of FLP and I-SceI enzymes, screening can be carried out by looking for animals that are resistant to the chemical, but which do not show GFP fluorescence. These would be individuals in which the resistance gene had segregated from the GFP donor chromosome marker gene. Targeting can be verified by molecular means. A positive-negative selection method can also be employed in such a screen to increase the sensitivity of recombinant detection.

Use in Other Animals.

Targeted alteration of animal genomes can be carried out using the procedures described herein.

Use in Cultured Tissues, Cells, Nuclei, or Gametes.

The method of the invention can also be applied in cultured cells or tissues, including those cells, tissues or nuclei that can be used to regenerate an intact organism, or in gametes, such as eggs or sperm in varying stages of their development.

It was demonstrated that an extrachromosomal DNA molecule with cut or broken ends that is generated in vivo, through the action of a site-specific recombinase (such as FLP) and site-specific endonuclease (such as I-SceI), is recombinogenic and can be employed for gene targeting. Alternatives for the representative embodiments described above are numerous, and not limited to the enzymes and constructs used to explain how the invention works.

Transposases can be used to generate the double strand (ds) break, substituting for the unique endonuclease, or to carry out the excision reaction, substituting for the recombinase. Many transposons, such as P elements in *Drosophila*, leave behind a ds break in DNA when they transpose. This property can be used to generate broken-ended extrachromosomal molecules for targeting. Examples are indicated below, but other possibilities also exist. These examples can be carried out using stably integrated transgene constructs as the source of the donor molecule (for instance, by placing the P element construct of Example 1 into a Mariner transposon and generating stably transformed *Drosophila*), or transient transgenes (for instance, the T-DNA example of Method 4, below). Transposase expression can occur by expression of endogenous transposons or variants thereof, by regulated or constitutive expression from engineered gene constructs that express transposase, by use of mRNA that encodes transposase, or by using the purified transposase protein. In plants, it may be advantageous to express the transposase and/or recombinase and/or site-specific endonuclease in the megaphone and micropore mother cells, just before or during meiosis. The freed DNA fragments can be designed for ends-in targeting (as shown in the Figures) or ends-out targeting. Genetic screening, selective methods, or molecular methods, can be used to recover the targeted recombinants.

Method 1: Using Two Copies of a Transposon.

A transgenic construct can be produced that carries two copies of a transposon (in this case, the P element of *Drosophila*) that flank the donor DNA. Recombinogenic donor DNA refers to the piece of DNA that is freed from the targeting construct as a broken-ended DNA molecule, and that is designed to cause homology-directed changes in a specific chromosomal locus. The transposition of the two transposons, simultaneously, will leave behind two ds breaks that flank the intervening DNA, freeing that fragment of DNA to recombine with the chromosome at the target site.

Method 2: Using a Site-specific Recombinase and a Transposase.

In this variation, a site-specific recombinase, such as FLP or Cre (or others known in the art), is used to free a segment of DNA that is flanked by recombinase recognition sites (such as FRTs or lox sites) from the donor construct. This freed DNA is circular in form. It will be converted to a linear form by transposition of a transposon from the circle, leaving behind a double strand break. The procedure can be simplified by using a transient or stable circular plasmid as the donor construct. Transposition of the transposon will leave a ds break behind in the plasmid. The plasmid is then recombinogenic and can be used for targeting, but with the disadvantage that vector sequences will be included in the donor DNA. However, these can be removed through the use of site-specific recombination or homologous recombination induced by a site-specific endonuclease.

Method 3: Use of Transposons to Free DNA From the Chromosome, and a Site-specific Endonuclease to Free a Donor from the Transposon.

A transposase can be used as an alternative to a recombinase to excise the donor construct from the donor site. For ends-out targeting, the donor gene construct is a linear construct, placed within the transposon. Using a transposase for excision, the transposase and I-SceI (or other unique endonuclease) can be expressed at approximately the same time. The fundamental concept relies on the excising of the transposon at the inverted repeats by the transposase, followed by cutting at the I-SceI sites with I-SceI. The combined action of the two enzymes creates a recombinogenic donor and is similar to what can be accomplished with a site-specific recombinase and site-specific endonuclease.

Method 4: Use of T-DNA.

A method similar to that described in Method 3 can be employed with T-DNA. The construct for this method is analogous to that of Method 3, except for the substitution of the respective T-DNA borders for the inverted repeats. This Method relies on I-SceI (or other unique endonucleases) being expressed in the transformed cells (for example, the egg cell in Arabidopsis). The idea is that in cells undergoing transformation, the T-DNA is cut by I-SceI, creating a recombinogenic donor.

Further explanation of the invention will be described by examination of various embodiments of the invention and reviewing various alternative means by which the invention can be carried out.

Method 5:

A method for forming an ends-out construct can be practiced. To form the construct, two pairs of oligonucleotides, which are I-SceI recognition sites: SEQ. ID. NOs. 1 and 2, and SEQ. ID. NOs. 3 and 4, are annealed and cloned into the plasmid. The resultant plasmid has two I-SceI recognition sites.

Next, primers SEQ. ED. NO. 5 and SEQ. ID. NO. 6 are used to add SphI termini to an FRT sequence (FLP recombinase target) by PCR. Primers SEQ. ID. NO. 7 and SEQ. ID. NO. 8 are used to add EcoRI termini to the FRT sequence by PCR.

As a template, a plasmid carrying a single copy of the FRT from the yeast 2μ-flanking DNA on each side is used. The amplified FRTs are cut with SphI and EcoRI endonucleases, respectively, and ligated into the SphI and EcoRI sites of the polylinker in the modified plasmid. Clones in which the two FRTs are in the same direction are selected. A vector, preferably a P element vector carrying a polylinker flanked by I-SceI sites adjacent to a selected gene was generated, with the FRTs adjacent to the I-SceI sites.

Method 6:

A method for forming an ends-out yellow disruption construct can be practiced. To form the construct, two oligonucleotides: SEQ. ID. NO. 9 and SEQ. ID. NO. 10 were annealed and cloned into the PstI site of a plasmid, for example, Carnegie 4. Using DNA sequencing, a plasmid can be chosen with the new sites inserted as (HindIII)XhoI-Acc65I-NotI-SphI(PstI-SalI), where sites in parentheses are already present in Carnegie 4.

Subsequently, two pairs of oligonucleotides, SEQ. ID. NOs. 11 and 12, and SEQ. ID NOs. 1 and 2 can be annealed and cloned into the SmaI and Acc65I sites of a polylinker, respectively, generating two I-SceI recognition sites.

PCR is used to add EcoRI termini to an FRT, as above. After digestion with EcoRI, the FRT was ligated into the EcoRI site of the polylinker. Then, a selected gene of a plasmid is removed as a PstI-SphI fragment and cloned into the sites of the polylinker.

An XhoI-flanked FRT is produced by using the primers SEQ. ID. NO. 13 and SEQ. ID. NO. 14 to amplify the FRT. After digestion with XhoI, it is ligated into the XhoI site of the polylinker. A clone whose two FRTs lay in the same direction is chosen, generating a vector, such as a P element vector carrying a selected gene flanked by I-SceI recognition sites, and FRTs outside of those. Unique sites of NotI and SphI upstream of the gene and BamHI downstream of the gene are available for cloning in the plasmid.

Primers SEQ. ID. NO. 15 and SEQ. ID. NO. 16 are used in the PCR with pS/G as template, to add NotI and SphI termini to a 3.05 kb yellow DNA fragment (from −3043 to −2 bp upstream of the start codon), which is then cloned into the sites of the plasmid.

Next, the oligos: SEQ. ID. NO. 17 and SEQ. ID. NO. 18 are annealed and cloned into the BamHI site of the polylinker, and the plasmid is selected whose BamHI site is next to the XbII site of the polylinker, generating BamHI-BsiWI-AscI sites in the polylinker. Primers SEQ. ID. NO. 19 and SEQ. ID. NO. 20 are used to add BsiWI and AscI termini to a DNA fragment (including part of the first exon and the intron and second exon) by PCR. This fragment is cloned into the corresponding sites downstream of the selected gene.

The use of ends-out targeting, also referred to as replacement or substitution type targeting, provides significant new capabilities for *Drosophila* genome modification. It gives a very direct route to the generation of a mutant allele. In a single step, the target gene can be disrupted by insertion of a marker gene within its coding region. The cloning steps are relatively simple because it is not necessary to engineer point mutations within the coding sequence of the gene, as is typically the case with ends-in targeting. Constructing donors to make deletions should also be straightforward: segments of DNA that flank, but do not include the target gene, are placed to the left and right of the marker gene in the donor construct. Homologous recombination then replaces the target gene with the marker gene.

One of the reasons that ends-out targeting is preferred in mouse ES cells is that it allows the application of positive-negative selection to enrich for targeted recombinants. In addition to the positively selectable marker gene within the target-homologous region, a negatively selectable marker gene is located outside the target-homologous DNA. Random integration tends to incorporate both genes, but homologous recombination excludes the negative marker. Applying both selections, simultaneously, greatly enriches for the targeted events. Because most donor insertion events in *Drosophila* are targeted, this is not needed. However, a positive-negative screening method could be used to facilitate recovery of targeting events in *Drosophila*. One marker gene, inserted in the targeting DNA, can be used to track mobilization of that segment, whereas a second marker gene, located outside the FRTs, would be left behind after FLP-mediated excision and would mark the donor chromosome. Segregation of these two markers would provide an easy screen to recover events in which donor DNA has transposed. Most of these would be legitimate targeting events.

EXAMPLES

To test whether ends-out targeting could be used in *Drosophila*, two strategies were applied for ends-out gene replacement at the endogenous yellow locus in *Drosophila*. First, a $y^1$ mutant allele was rescued by replacement with an 8 kb $y^+$DNA fragment: yellow rescue events were recovered at a rate of about 1/800 gametes. Second, a wildtype $y^+$gene was disrupted by the insertion of a $w^+$marker gene in exon 1: yellow disruption events were recovered at a rate of approximately 1/380 gametes. It was observed that ends-out targeting can be approximately as efficient as ends-in targeting, and is likely to be generally useful for *Drosophila* gene targeting.

Example 1

An ends-out donor rescue construct was formed as follows:

Two pairs of oligonucleotides, which were I-SceI recognition sites: SEQ. ID. NOs. 1 and 2, and SEQ. ID. NOs. 3 and 4, were annealed and cloned into the Acc65I and PstI sites of plasmid, pw8 (10). As such, the pw8 plasmid had two I-SceI recognition sites inserted therein. Next, primers SEQ. ID. NO. 5 and SEQ. ID. NO. 6 were used to add SphI termini to an FRT sequence (FLP recombinase target) by PCR. Primers SEQ. ID. NO. 7 and SEQ. ID. NO. 8 were used to add EcoRI termini to the FRT sequence by PCR.

As a template, a plasmid carrying a single copy of the FRT from the yeast 2μ plasmid, with approximately 300 bp of 2μ-flanking DNA on each side was used. The amplified FRTs were cut with SphI and EcoRI endonucleases, respectively, and ligated into the SphI and EcoRI sites of the polylinker in the modified plasmid pw8. Clones were chosen in which the two FRTs were in the same direction, generating the vector pw30, a P element vector carrying a polylinker flanked by I-SceI sites, with the FRTs, adjacent to a $w^+$ gene.

pw30 was cut with XhoI, and an 8 kb SalI $y^+$ genomic fragment from pS/G (11) was cloned into that site.

Example 2

An ends-out yellow disruption construct was formed as follows:

Two oligonucleotides: SEQ. ID. NO. 9 and SEQ. ID. NO. 10 were annealed and cloned into the PstI site of Carnegie 4 (12). By DNA sequencing, a plasmid was chosen with the new sites inserted as (HindIII)XhoI-Acc65I-NotI-SphI(PstI-SalI), where sites in parentheses were already present in Carnegie 4.

Subsequently, two pairs of oligonucleotides, SEQ. ID. NOs. 11 and 12, and SEQ. ID. NOs. 1 and 2 were annealed, and cloned into the SmaI and Acc65I sites of a polylinker, respectively, generating two I-SceI recognition sites.

PCR was used to add EcoRI termini to an FRT, as above. After digestion with EcoRI, the FRT was ligated into the EcoRI site of the polylinker. Then, a $w^+$ gene of pw6 (10) was removed as a PstI-SphI fragment and cloned into the sites of the polylinker.

An XhoI-flanked FRT was produced by using the primers SEQ. ID. NO. 13 and SEQ. ID. NO. 14 to amplify the FRT. After digestion with XhoI, it was ligated into the XhoI site of the polylinker. A clone whose two FRTs lay in the same direction was chosen, generating the vector pw35: a P element vector that carried a white gene flanked by I-SceI recognition sites, and FRTs outside of those. Unique sites of NotI and SphI upstream of white and BamHI downstream of white were available for cloning in pw35.

Primers SEQ. ID. NO. 15 and SEQ. ID. NO. 16 were used in the PCR with pS/G as template, to add NotI and SphI termini to a 3.05 kb yellow DNA fragment (from −3043 to −2 bp upstream of the start codon), which was then cloned into those sites of pw35.

Next, the oligos: SEQ. ID. NO. 17 and SEQ. ID. NO. 18 were annealed and cloned into the BamHI site of the polylinker, and the plasmid was selected whose BamHI site was next to the XbII site of the polylinker, generating BamHI-BsiWI-AscI sites in the polylinker. Primers SEQ. ID. NO. 19 and SEQ. ID. NO. 20 were used to add BsiWI and AscI termini to a 4.77 kb yellow DNA fragment (including part of the first exon and the intron and second exon) by PCR. This yellow fragment was cloned into the corresponding sites downstream of $w^+$.

Example 3

A yellow rescue construct without FRTs was formed. Two pairs of oligos: SEQ. ID. NOs. 21 and 22, and SEQ. ID. NOs. 3 and 4 were annealed and cloned into the EcoRI and PstI sites of pw8, respectively, destroying the two restriction sites and creating two I-SceI recognition sites. Then, the 8 kb SalI $y^+$ fragment was cloned into the XhoI site of this vector.

Example 4

A mutation rescue procedure was performed using the construct of Example 1. First, an enzyme construct was formed. Heat-inducible FLP recombinase (13) and I-SceI endonuclease (9) transgenes (70FLP and 70I-SceI) were the two enzyme constructs used. The enzyme constructs were formed according to known procedures. A heat-inducible I-SceI gene (70I-SceI) was constructed and a standard P element transformation was used to generate fly lines carrying the transgene (14).

A screen for targeted rescue of $y^1$ was conducted by producing flies that carried a heat-inducible FLP gene (70FLP), 70I-SceI, and the donor construct of FIG. 1C (28).

The $y^+$ P element donor construct of Example 1 was transformed to rescue $y^1$, which has a mutation in its first codon. The construct consisted of a $y^+$ gene flanked by I-SceI recognition sequences and FLP Recombination Targets (FRTs), adjacent to a $w^+$ gene that lies outside the FRTs (FIG. 2A). It was transformed by the standard P-mediated method (Spradling). For targeting, FLP and I-SceI expression were induced to excise $y^+$ from the chromosome and to generate the DSBs that stimulate homologous recombination.

Figure 3:
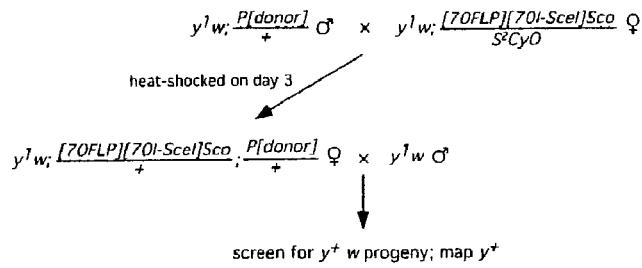
FIG. 3 is a diagram of the crossing schemes disclosed herein, with the crosses used for the rescue and disruption experiments shown, in the yellow rescue experiments, females with pigmented eyes were selected for the second cross, ensuring that all progeny females carried the donor, for the disruption crosses, in some cases, the donor element was homozygous in the males and so only half of the females used in the second cross carried the donor, the targeting frequency was adjusted accordingly in Table 1, in other cases, females exhibiting some degree of pigmentation in the eye were selected, ensuring that they carried the donor, or the males used in the first cross carried the donor heterozygous with a dominantly-marked balancer chromosome, thus allowing the selection of females that carried the donor for the second cross.
Figure 3:
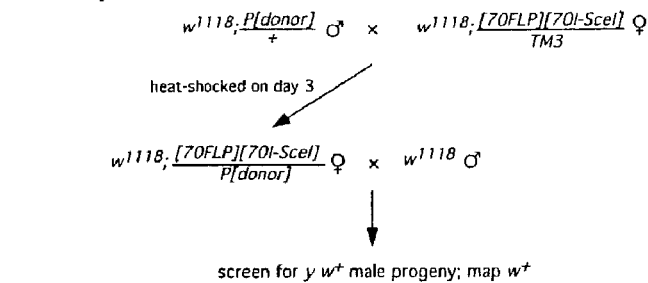

Testcrosses were carried out, as diagrammed in FIG. 3, and screened for $y^+$ w progeny to recover events that converted the endogenous $y^1$ allele to $y^+$. In other words, $y^+$ was screened for to move from its original location, next to the $w^+$ gene on an auto some, to the X chromosome, and then segregate from the $w^+$ gene in meiosis.

Figure 4:
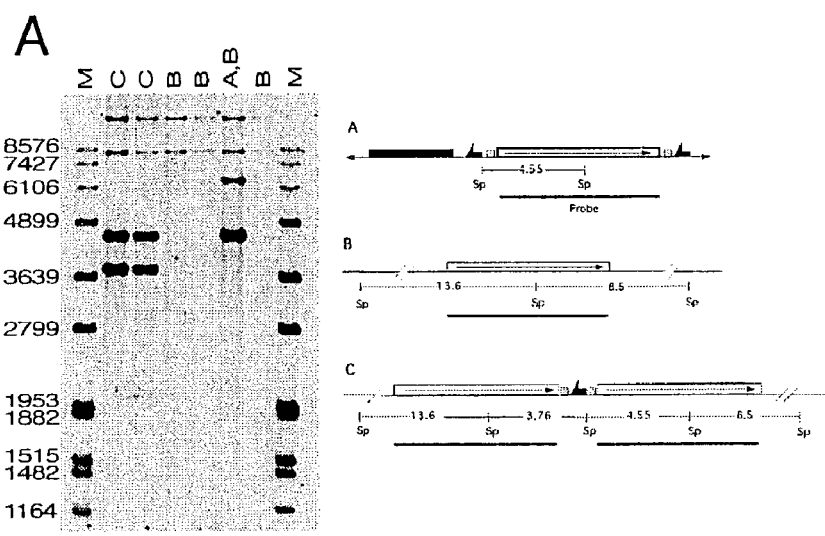
FIG. 4 relates to verification of targeting: Section (A) shows genomic Southern blotting used to verify targeted yellow rescue, the expected structures of the donor construct, the yellow target gene (which is unchanged after the expected single-copy rescue event), and a tandem rescue event are indicated to the right, the lettering indicates the type of fly whose genomic DNA was examined in each lane, the region used as a probe is indicated as a solid line below each structure, along with the expected sizes of the fragments produced by SphI (Sp) digestion, the left and right lanes (M) carry molecular weight markers with sizes indicated at the left; Section (B) shows cytological verification of targeted disruption, the white gene was used as a probe on polytene chromosomes of a larva carrying a putative targeting event shows the two sites of hybridization, and their cytological designations, are indicated; and, Section (C) shows genomic Southern blotting to verify targeted yellow disruption, the expected structures of the target locus, the donor construct, a single-insert targeted allele, and a tandem-insert targeted allele are indicated to the right, along with the expected sizes of bands produced by SalI (S) digestion; and, FIG. 5 shows the efficiency of donor generation, whereby flies carrying donor constructs and 70I-SceI (A and B), or 70FLP and 70I-SceI (C) were heat shocked at 38° C. for 1 hour, the genomic DNA was prepared at various times after heat shock (indicated in hours above the lanes); Section (A) shows assay of DSBs at the I-SceI sites in the cut-only rescue construct, the genomic DNA was digested with EcoRI, the 6.3/6.1 kb doublet is shown at a reduced exposure at the bottom; Section (B) shows genomic DNA from larvae carrying 70I-SceI and the cut-only construct, blotted without restriction digestion, the film was overexposed to visualize the linear donor freed by I-SceI digestion; Section (C) shows genomic DNA from larvae carrying 70FLP and 70I-SceI and the yellow rescue construct with FRTs, blotted without restriction digestion, RC, relaxed circle, 1CL, single-cut linear, 2CL, double-cut linear, SC, super-coiled circle; Section (D) shows the structures of the endogenous yellow gene and the two donor constructs, all blots were probed with the 8 kb yellow probe indicated by the solid bar beneath the yellow gene, in the rescue construct, a single FRT adds approximately 250 bp. R, EcoRI; -HS, not heat-shocked; MW, molecular weight markers.
Figure 4:
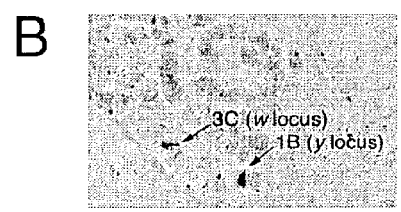
Figure 4:
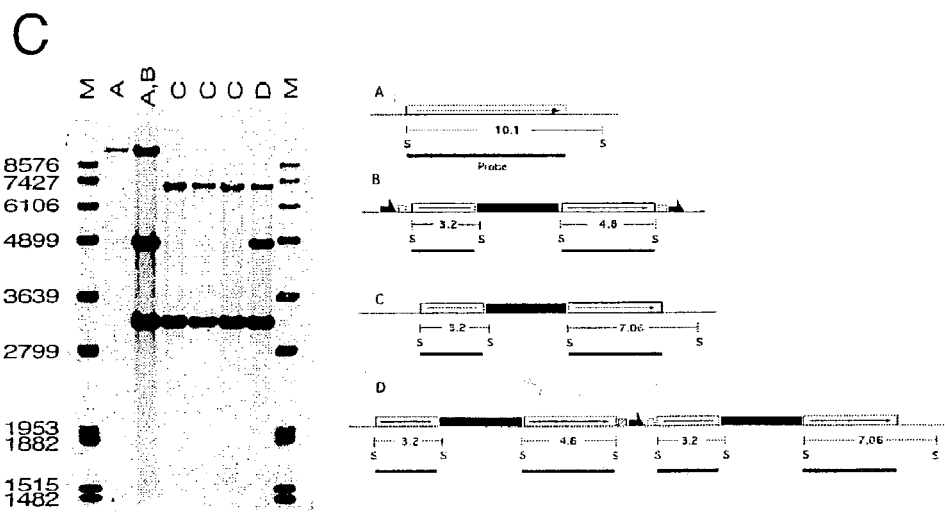

In the present example, $y^+$ was efficiently excised from the donor chromosome, with almost all $w^+$ progeny showing loss of $y^+$, (33,668/33,790=99.6% in 772 vials counted). A total of 43 independent targeting events that converted $y^1$ into $y^+$were recovered at an average rate of approximately one independent event per 16 vials screened (unweighted; Table 1). Each vial produced approximately 52 white-eyed progeny, translating to 1 targeting event in 832 gametes. Four independent non-targeted $y^+$ w events were also recovered. In these, $y^+$ did not map to the X, and they were not examined further. They may have included insertion of $y^+$ at other locations, or loss of $w^+$ from the donor construct after an I-SceI cut, without excision of $y^+$. In any event, targeted recombination events outnumbered non-targeted events by better than 10:1. Targeting was confirmed by Southern blotting (FIG. 4A).

TABLE 1

Recovery of Targeting Events.

| FLP 1-SceI | donor[1] | n | T | NT |
|---|---|---|---|---|
| Rescue Construct (FIG. 2A) | | | | |
| on 2 | 1A (3) | 652 | 22 | 1 |
| on 2 | 2A (2) | 147 | 10 | 2 |
| on 3 | 2A (2) | 135 | 11 | 1 |
| Disruption Construct (FIG. 2B) | | | | |
| on 3 | 6C[2](3) | 147 | 48 | 0 |
| on 3 | 5C[2](3) | 79 | 29 | 0 |
| on 2 | 5C (3) | 99 | 14 | 0 |
| on 2 | 4A (3) | 90 | 8 | 0 |
| on 3 | 4A (3) | 84 | 7 | 0 |
| Rescue (FIG. 2C) | | | | |
| on 2 | 43 (3) | 131 | 0 | 0 |
| on 3 | 43 (3) | 116 | 0 | 0 |
| Disruption Construct (FIG. 2B, but using I-SceI expression only) | | | | |
| on 3 | 6C (3) | 112 | 0 | 0 |
| on 3 | 5C (3) | 120 | 0 | 0 | n = number of vials scored for targeting;
T = number of vials with targeting events, which is taken to be the minimum estimate of independent targeting events;
NT = number of vials with non-targeted events
[1]The chromosome bearing the donor is indicated in parentheses.
[2]Only half of the tested females carried the donor. The number of vials tested has been multiplied by 0.5 to correct. Each vial contained 4–7 pairs of heat-shocked females and males.

The majority of targeting events resulted from a straightforward replacement of $y^1$ with $y^+$, but approximately 20% (9/43) had two copies of the yellow gene at the target locus. Integration of donor dimers has been seen previously with ends-in targeting in yeast and flies (15, 3, 16), and ends-out targeting in mouse ES cells (17, 4, 18). Concatemer formation between multiple copies of the donor appears to be the cause. The flies used in this experiment carried a single copy of the donor P element (verified by Southern blotting). However, in G2 of the cell cycle, two copies were present on the replicated chromatids, providing the opportunity for two donors to dimerize by FLP-mediated or homologous recombination, or by non-homologous end-joining, and undergo targeting.

As such, the donor construct was proven a sufficient candidate as a rescue construct. The Example demonstrates the feasibility of ends-out replacement.

Example 5

The present Example relates to gene disruption, with the plasmid of Example 2 used. These results further demonstrate the feasibility of ends-out gene targeting in *Drosophila*. To extend this method to generate mutant alleles of target genes, a donor element carrying the yellow gene disrupted by the insertion of a $w^+$ gene (FIG. 2B) was formed. Approximately 50 bp of y coding sequence, including the start codon, were eliminated in the construction. Targeting with this construct is expected to generate a mutant y allele and carry $w^+$ into the locus.

Disruption of the endogenous $y^+$ gene in a $y^+$ w background, by using donors on chromosome 3, was screened for, as well as looking for y $w^+$ progeny by test-crossing (FIG. 3). As in the previous experiments, excision of the donor was very efficient (>99%), as judged by loss of $w^+$. Recovery of 106 independent targeting events was done at a rate of approximately 1 in 5 vials (unweighted average; Table 1). Each vial produced approximately 76 male offspring, or 1 targeting event in 380 gametes. In every case, the $w^+$ gene mapped to the X chromosome as expected for targeting at yellow. Four lines were examined by chromosomal in situ hybridization, and in all four, the white gene sequence was detected at its normal location of 3C on the X chromosome, and also at 1B, the normal location of yellow, confirming that targeted recombination had integrated $w^+$ at the target locus (FIG. 4B). Southern blotting of 89 cases confirmed that all resulted from targeted homologous recombination at yellow (FIG. 4C). As in the previous experiments, some duplicated alleles were recovered, but at a lower rate (2/89).

In these crosses screening was done for disruption of $y^+$ and integration of $w^+$ simultaneously. Only targeted events were recovered. The ends-out construct was observed to effectively insert the selected gene in the host. This is important because in most cases, the mutant phenotype of the target gene will not likely be known. Also, related to this, it is easier to recover targeting events by screening only for mobilization of $w^+$. In three previous sets of studies using a variety of target genes (3, 19, 16), and additionally with the yellow rescue experiments reported above, it was seen that donor integration in females occurred mostly at the target locus. As such, it was expected that the majority of the events detected by $w^+$ mobilization would be inserted at the target locus. Thus, the construct demonstrates its suitability for gene targeting.

Example 6

The present Example was conducted to determine whether gene targeting requires FLP. Because I-SceI cuts with high efficiency, it was reasoned that a $y^+$ gene could be readily liberated from the chromosome by two I-SceI cuts. The freed gene could then act as the donor to convert the endogenous $y^1$ to $y^+$. This is the construct of Example 3. A construct was built similar to the first rescue construct, but without FRTs (FIG. 2C). This is the construct of Example 3. A donor insertion on chromosome 3 was used to detect yellow rescue by testcrossing heat-shocked females that carried the donor and 70I-SceI genes. As with the previous yellow rescue experiment, it was expected to see targeting events as $y^+$ w flies resulting from independent assortment of the y+and w+genes. It was observed that there were no targeting events in 247 vials (Table 1). Surprisingly, y $w^+$ flies were very rare among the $w^+$ offspring (10/1154 from 22 vials counted=0.9% of all $w^+$ progeny), though it was expected that they would be frequent as a result of excision and loss of $y^+$.

Two possible explanations follow. One possibility supposes that repair of the cut chromosomal ends was very inefficient, and even though targeting might have occurred, the cells in which it did occur died because of a failure to fix the chromosomal double strand break (DSB) at the donor site. Alternatively, repair of a DSB generated by I-SceI may be extremely efficient so that it is very rare for both I-SceI sites to be cut at the same time, which was necessary to generate the extrachromosomal donor.

Figure 5:
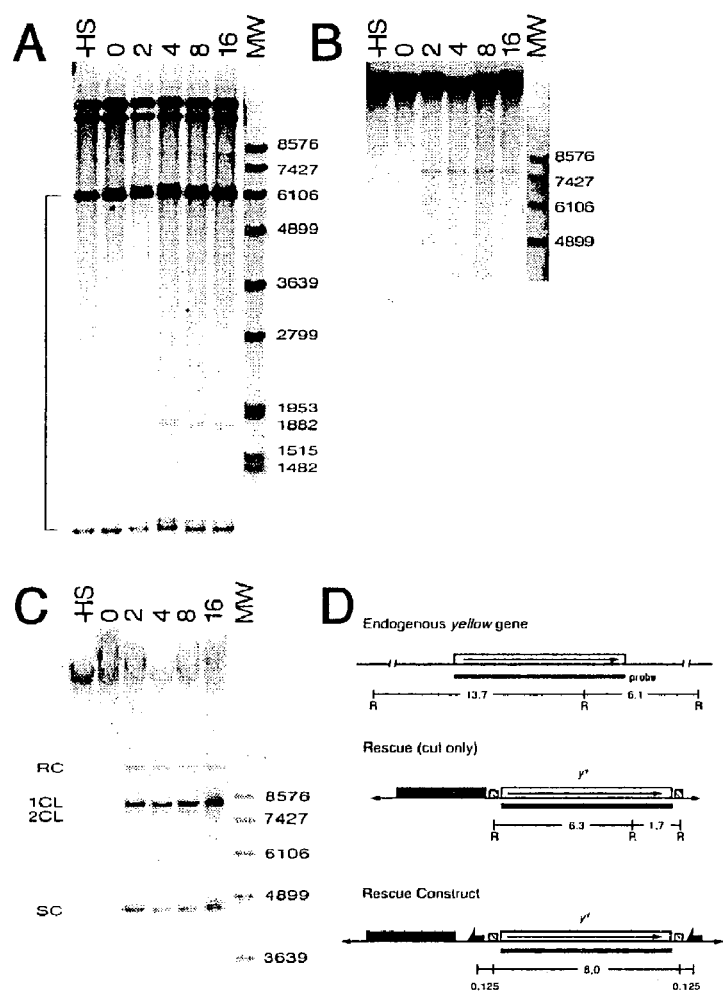

To distinguish these possibilities, a physical analysis was carried out of cutting at the I-SceI sites. Second and third instar larvae were heat shocked at 38° C. for 1 hour, and genomic DNA was prepared from samples of these larvae at various times after the heat shock. The genomic DNA was digested with EcoRI (which cut once within the yellow gene), and after electrophoretic separation and Southern blotting, probed with they gene clone to assess the presence of DSBs within the donor element (FIG. 5A). A cut at site 1 was expected to generate a 6.3 kb fragment on this gel, a cut at site 3 would generate a 1.7 kb fragment. This experiment was carried out with a mixture of male and female larvae that were heterozygous for the donor element: 60% of the total yellow signal derives from the endogenous yellow gene with ban sizes of 13.7 and 6.1 kb; the remaining 40% came from the donor. By scanning of the exposed film, an estimate of the approximate proportion of the donor with a DSB at each site was made. At the peak of cutting, about 4 hours after HS, approximately 30% of the donor exhibited a DSB at site 1 and approximately 5% at site 2. This predicts that only 1-2% of donor elements have two DSBs at the same time. To confirm this, we carried out blotting and hybridization with undigested genomic DNA from the same experiment (FIG. 5B) was conducted. Although the extrachromosomal linear form of the donor DNA does appear, it is very infrequent and constitutes approximately 7% of the total donor DNA at its peak of approximately 8 hours after heat shock.

Thus, it appears that the extrachromosomal donor element was infrequently produced by I-SceI cutting, and, at its peak, only 2-7% of the donor element existed in this form. Before concluding that the failure to obtain targeting with I-SceI, alone, is a consequence of the short time for I-SceI generated DSBs, alternative explanations were tested for the scarcity of the free donor.

Although a variety of tests led to the conclusion that cutting at I-SceI sites, after heat shock induction of 70I-SceI, is generally highly efficient in *Drosophila*, showing 90% or better rates of cutting (3; unpublished results), it is still possible that cutting at the I-SceI sites of this second rescue construct is inefficient in this context. If the failure to obtain targeting is solely because this construct is inefficiently cut, relative to constructs with successful targeting, then it seemed reasonable to expect that targeting could succeed by using I-SceI, and not FLP, with the $y^+$ disruption construct. Accordingly donors 5C and 6C of the disruption construct were tested for targeting using I-SceI expression, alone. No targeting events were obtained in 232 vials (Table 1), though we would have expected less than 60 if targeting occurred as efficiently as it did when FLP was also used with these same donors. It was concluded that the failure to obtain targeting when using only I-SceI cannot be solely attributed to inefficient cutting of the I-SceI sites.

Another explanation for the absence of a significant band representing the linear donor on the blot of FIG. 5B was that, though it might have been efficiently produced, it was also efficiently degraded. The results presented argued against this. For instance, no significant reduction was seen in the quantity of donor hybridizing material during the course of the experiment. Furthermore, if extrachromosomal donor molecules were efficiently generated, targeting should have been seen when I-SceI and the disruption construct was used. Nonetheless, to test this possibility more directly, the generation of extrachromosomal donor was examined after expression of FLP and I-SceI in larvae carrying the first yellow rescue construct. By Southern blotting of genomic DNA prepared without further digestion (FIG. 5C), it was seen that the extrachromosomal form of the donor appeared rapidly or, within two hours, the majority of donor was found out of the chromosome (not shown) in four bands. These probably represented relaxed circles, single and double cut linear forms, and supercoiled circles. At all time points, from two hours after heat shock and beyond, more than 50% of the extrachromosomal donor was found in the linear form. Since FLP-mediated excision was nearly 100% efficient, it followed that extrachromosomal linear donor molecules were generated much more efficiently by FLP and I-SceI than by I-SceI by itself. Moreover, these results clearly showed that the extrachromosomal form could persist for many hours, even when the majority had experienced double-strand breaks. These results exclude the explanation that the extrachromosomal donor was not detected following I-SceI expression alone because it was rapidly degraded.

The most likely explanation for failed targeting with I-SceI expression alone is that the I-SceI-generated breaks were rapidly and efficiently repaired, and there was only a small chance of having both sites cut simultaneously to free the donor. If an unrepaired DSB in the chromosome was to persist for a lengthy period of time, it was expected that it would lead to somatic cell death, and be accompanied by the characteristic phenotypes of such cell death. Flies carrying 70I-SceI and the second yellow rescue construct were heat-shocked (with only I-SceI sites and no FRTs) at 3, 4, and 5 days after egg-laying, and none of the phenotypes that were characteristic of the cell death resulting from an unrepaired DSB (20, 21) were observed. None of the phenotypes that were characteristic of the cell death resulting from an unrepaired DSB (20, 21) were observed. Yellow and white somatic mosaicism was seen in the flies, which confirmed that I-SceI worked. The mosaic phenotypes most likely resulted from degradation of cut ends followed by non-homologous end joining in a fraction of the soma. There appeared to be a significant component of relaxed extrachromosomal circles in FIG. 5C, as though the excised superhelical circles had been cut, and then repaired. It was expected that the yellow gene was excised as a supercoiled circle (22), but cutting and repair could release the supercoils to produce a relaxed circle. This would be consistent with the idea that the DSBs, although efficiently generated, were rapidly repaired.

The results did not rule out the possibility that targeting could occur by I-SceI cutting only, for a small fraction of freed donor was detected. But, if it could occur, it would clearly be a much less efficient process than when FLP was used to excise the donor from its chromosomal site.

Example 7

In relation to the above Examples, crosses for targeting were carried out in standard 25 mm diameter vials, with 3-6 females per vial and a corresponding number of the appropriate males. Heat shocks were performed in a circulating water bath, as previously described (13). All constructs were transformed into the germline of *Drosophila melanogaster* using standard methods (14).

Example 8

The Southern blotting method discussed in the previous Examples is listed herefroth. For verification of targeting, DNA was prepared from males carrying the targeted yellow allele. For analysis of I-SceI cutting in vivo, genomic DNA was prepared from larvae, either 0, 2, 4, 8, or 16 hours after heat shock, and from larvae that had not been heat shocked. The genomic DNAs were digested as indicated, separated by agarose gel electrophoresis, and transferred to nylon membranes. The membranes were probed with a Dig-labeled 8 kb SalI yellow DNA fragment from pS/G, and hybridization was detected by chemiluminescence using the DIG system (Roche).

Thus, there has been shown and described a gene targeting method which fulfills all the objects and advantages sought therefor. It is apparent to those skilled in the art, however, that many changes, variations, modifications, and other uses and applications to the gene targeting method are possible, and also such changes, variations, modifications, and other uses and applications which do not depart from the spirit and scope of the invention are deemed to be covered by the invention, which is limited only by the claims which follow.

REFERENCES

1. Rothstein, R. (1991) *Methods Enzymol.* 194,281-301.
2. Muller, U. (1999) *Mech Dev.* 82, 3-21.
3. Rong, Y. S. & Golic, K. G. (2000) *Science* 288, 2013-2018.
4. Hasty, P., Rivera-Perez, J., Chang, C. & Bradley, A. (1991) *Mol. Cell Biol.* 11, 4509-4517.
5. Hastings, P. J., McGill, C., Shafer, B. & Strathern, J. N. (1993) *Genetics* 135, 973-980.
6. Leung, W. -Y., Malkova, A. & Haber, J. E. (1997) *Genetics* 94, 6851-6856.
7. Thomas, K. R. & Capecchi, M. R. (1987) *Cell* 51, 503-512.
8. Deng, C. & Capecchi, M. R. (1992) *Mol. Cell Biol.* 12, 3365-3371.
9. Bellaiche, Y., Mogila, V. & Perrimon, N. (1999) *Genetics* 152, 1037-1044.
10. Klemenz, R., Weber, U. & Gehring, W. J. (1987) *Nucleic Acids Res.* 15, 3947-3959.
11. Geyer, P. K. & Corces, V. G. (1987) *Genes Dev.* 1, 996-1004.
12. Rubin, G. M. & Spradling, A. C. (1983) *Nucleic Acids Res.* 11, 6341-6351.
13. Golic, K. G. & Lindquist, S. (1989) *Cell* 59, 499-509.
14. Rubin, G. M. & Spradling, A. C. (1982) *Science* 218, 348-353.
15. Orr-Weaver, T., Szostak, J. W. & Rothstein, R. J. (1981) *PNAS USA* 78, 6354-6358.
16. Rong, Y. S., Titen, S. W., Xie, H. B., Golic, M. M., Bastiani, M., Bandyopahdyay, P., Olivera, B. M., Brodsky, M., Rubin, G. M. & Golic, K. G. (2002) *Genes Dev.* 16, 1568-1581.
17. Scwartzberg, P. L., Robertson, E. & Goff, S. P. (1990) *PNAS USA* 87, 3210-3214.
18. Thomas, K. R., Deng, C. & Capecchi, M. R. (1992) *Mol. Cell. Biol.* 12, 2919-2923.
19. Rong, Y. S. & Golic, K. G. (2001) *Genetics* 157, 1307-1312.
20. Golic, K. G. (1994) *Genetics* 137, 551-563.
21. Ahmad, K. & Golic, K. G. (1999) *Genetics* 151, 1041-1055.
22. Fitzgerald, D. P. & Bender, W. (2001) *Mol. Cell. Biol.* 21, 6585-6597.
23. Seum, C., Pauli, D., Delattre, M., Jaquet, Y., Spierer, A. & Spierer, P. (2002) *Genetics* 161, 1125-1136.
24. Michiels, F., Gasch, A., Kaltschmidt, B., & Renkawitz-Pohl, R. (1989) *EMBO J* 8, 1559-65.
25. Bonner, J. J., Parks, C., Parker-Thornburg, J., Mortin, M. A. & Pelham, H. R. B. (1984) *Cell* 37, 979-991.
26. Golic, M. M. & Golic K. G. (1996) *Genetics* 143, 385-400.
27. Golic, M. M., Rong, Y. S., Petersen, R. B., Lindquist, S. L. & Golic, K. G. (1997) *Nucleic Acids. Res.* 25, 3665-3671.
28. Surosky, R. & Tye, B. -K. (1985) *PNAS UAS* 82,2106-2110.
29. Matzuk, M. M., Finegold, M. J., Su, J. G., Hsueh, A. J. & Bradley, A. (1992) *Nature* 360, 313-319.
30. Dale, E. C. & Ow, D. W. (1991) *PNAS USA* 88, 10558-10562.
31. Gu, H., Marth, J. D., Orban, P. C., Mossman, H. & Rajewsky, K. (1994) *Science* 265, 103-106.
32. Meyers, E. N., Lewandowski, M. & Martin, G. R. (1998) *Nat. Genet.* 18, 136-141.
33. Bunting, M., Bernstein, K. E., Greer, J. M., Capecchi, M. R. & Thomas, K. R. (1999) *Genes Dev.* 13, 1524-28.
34. Siegal, M. L. & Hartl, D. L. (1996) *Genetics* 144, 715-726.
35. Mansour, S. L., Thomas, K. R. & Capecchi, M. R. (1988) *Nature* 336, 348-352.
36. Gloor, G. B., et al. (1991) *Science* 253:1110-1117.
37. Capecchi, M. R. (1989) *Trends in Genetics* 5:70-76.
38. Bronson, S. K. (1994) *J. Biol. Chem.* 269:27155-27158.
39. McCreath, K. J., et al. (2000) *Nature* 405:1066-1069.
40. Sauer, B., et al. (1994) *Current Opinion in Biotech.* 5:521-527.
41. Sargent, R. G., et al. (1997) *Mol. Cell. Biol.* 17:267-277.
42. Liang, F., et al. (1998) *Proc. Natl. Acad. Sci. USA* 95:5172-5177.
43. Cohen-Tannoudji, M. et al. (1998) *Mol. Cell. Biol.* 18:1444-1448.
44. Belfort, M., et al. (1997) *Nucl. Acids. Res.* 25:3379-3388.
45. Nunes-Duby, S., et al. (1998) *Nucleic Acids Res.* 26:391-406.
46. Craig, N. L. K. (1988) *Ann. Rev. Genet.* 22:77.
47. Cox, M. M. FLP site-specific recombination system of *Saccharomyces cerevisiae* (1988) *Gen. Recomb.* (R. Kucherlapati and G. R. Smith, eds.) *American Society for Microbiology*, Washington, D.C. 429-443.
48. Hoess, R. H., et al. (1990) *Nucl. Acid and Molec. Biol. Vol.* 4, 99-109.
49. Catteruccia, F., et al. (2000) *Nature* 405:954-962.
50. Haren, et al. (1999) *Annu. Rev. Microbiol.* 53:245-281.
51. Reznifoff, et al. (1999) *Biochem. Biophys. Res. Commun.* December 29:266(3); 729-734.
52. Ivics, et al. (1999) 60:99-131.
53. Weinberg (1998) March 26:8(7):R244-247.
54. HALLET, BERNARD et al., Transposition and Site-specific recombination: adapting DNA cut-and-paste mechanisms to a variety of genetic rearrangements, (1997) *FEMS Microbiol. Rev.* Vol. 21, p. 157-178.
55. Craig (1997) *Annu. Rev. Biochem.* 66:437-474.
56. Beall, et al. (1997) *Genes Dev.* August 15:11(16):2137-2151.
57. Polejaeva, I. A., et al. (2000) *Nature* 407:86-90.
58. Shulman, M. J., et al. (1990) *Mol. Cell. Biol.* 10:466.
59. Scheeber, J. B. & Adair, G. M. (1994) *Mol. Cell. Biol.* 14:6663.
60. Dray, T. & Gloor, H. G. B. (1997) *Genetics* 147:684.
61. Golic, M. M. (1997) *Nucleic Acid Res.* 25:3665.
62. Handler, A. M. & James, A. A. eds. *Insect Transgenesis Methods & Applications* (2000) CRC Press, Boca Raton, Fla.

What is claimed is:

1. A method of gene targeting in *Drosophila* comprising:
   (a) selecting a *Drosophila* target gene;
   (b) providing a donor construct comprising a transposon and a DNA segment homologous to the target gene comprising a marker sequence, wherein the DNA segment is flanked at both ends by a rare-cutting endonuclease recognition site and additionally flanked by a recombinase recognition site;
   (c) introducing the donor construct to a female *Drosophila* to obtain a transgenic female *Drosophila* whose genome comprises the transposon and the DNA segment flanked by said rare-cutting endonuclease recognition sites and said recombinase recognition sites;
   (d) providing a construct comprising a DNA sequence encoding a rare-cutting endonuclease and a DNA sequence encoding a recombinase, wherein each DNA sequence is operably linked to an inducible promoter;

(e) introducing the construct of step (d) to a male *Drosophila* to obtain a transgenic male *Drosophila* whose genome comprises a DNA sequence encoding the rare-cutting endonuclease and a DNA sequence encoding the recombinase, wherein each DNA sequence is operably linked to an inducible promoter;

(f) crossing the male transgenic *Drosophila* and the female transgenic *Drosophila* to produce progeny whose genome comprises the transposon and the DNA segment flanked by the rare-cutting endonuclease recognition sites and recombinase recognition sites, and whose genome also comprises a DNA sequence encoding the rare-cutting endonuclease and a DNA sequence encoding the recombinase, wherein each DNA sequence is operably linked to an inducible promoter;

(g) activating the inducible promoter in the progeny of step (f) to express the rare-cutting endonuclease and the recombinase such that recombination occurs between the target gene and the target construct; and (h) selecting a transgenic progeny whose genome comprises the disrupted target gene.

2. The method of claim 1, wherein the inducible promoter is a heat shock promoter.

3. The method of claim 2, wherein the heat shock promoter is the heat shock 70 (hsp70) promoter.

4. The method of claim 1, wherein the endonuclease is selected from the group consisting of I-SceI, I-TliI, I-CeuI, I-PpoI, I-CreI, and PI-PspI.

5. The method of claim 1, wherein the recombinase and its specific recognition site, respectively, are selected from the group consisting of the Cre and lox recombination system and the FLP and FRT recombination system.

6. The method of claim 1, wherein the donor construct comprises DNA encoding one or more selectable markers.

7. The method of claim 6, wherein the selectable marker provides positive selection for cells expressing the marker.

8. The method of claim 6, wherein the selectable marker provides negative selection against cells expressing the marker.

9. The method of claim 6, wherein the selectable markers provide positive and negative selection of cells expressing the markers.

10. The method of claim 1, wherein the donor construct comprises DNA encoding a screenable marker.

11. The method of claim 10, wherein the screenable marker is selected from the group consisting of beta-glucuronidase, green fluorescent protein, and Lucifers.

* * * * *

SEQUENCE LISTING

<160> NUMBER OF SEQ ID NOS: 22

<210> SEQ ID NO 1
<211> LENGTH: 22
<212> TYPE: DNA
<213> ORGANISM: Drosophila acanthoptera

<400> SEQUENCE: 1
gtacattacc ctgttatccc ta                                            22

<210> SEQ ID NO 2
<211> LENGTH: 22
<212> TYPE: DNA
<213> ORGANISM: Drosophila acanthoptera

<400> SEQUENCE: 2
gtactaggga taacagggta at                                            22

<210> SEQ ID NO 3
<211> LENGTH: 22
<212> TYPE: DNA
<213> ORGANISM: Drosophila acanthoptera

<400> SEQUENCE: 3
tagggataac agggtaattg ca                                            22

<210> SEQ ID NO 4
<211> LENGTH: 22
<212> TYPE: DNA
<213> ORGANISM: Drosophila acanthoptera

<400> SEQUENCE: 4
attaccctgt tatccctatg ca                                            22

<210> SEQ ID NO 5
<211> LENGTH: 43
<212> TYPE: DNA
<213> ORGANISM: Drosophila acanthoptera

<400> SEQUENCE: 5
gagaaaggat ccaagcatgc tgcgacgtga acagtgagct gta                     43

<210> SEQ ID NO 6
<211> LENGTH: 49
<212> TYPE: DNA
<213> ORGANISM: Drosophila acanthoptera

<400> SEQUENCE: 6
gttagaggat ccccgcatgc agctcgttac agtccggtgc gtttttggt              49

<210> SEQ ID NO 7
<211> LENGTH: 36
<212> TYPE: DNA
<213> ORGANISM: Drosophila acanthoptera

<400> SEQUENCE: 7
gtcatagaat tcacgcacta tgccgttctt ctcatg                             36

<210> SEQ ID NO 8
<211> LENGTH: 35
<212> TYPE: DNA
<213> ORGANISM: Drosophila acanthoptera

```
<400> SEQUENCE: 8
gagcatgaat tcgtttgtgg aagcggtatt cgcaa                          35

<210> SEQ ID NO 9
<211> LENGTH: 31
<212> TYPE: DNA
<213> ORGANISM: Drosophila acanthoptera

<400> SEQUENCE: 9
ctcgagggta ccgcggccgc gcatgcctgc a                              31

<210> SEQ ID NO 10
<211> LENGTH: 31
<212> TYPE: DNA
<213> ORGANISM: Drosophila acanthoptera

<400> SEQUENCE: 10
ggcatgcgcg gccgcggtac cctcgagtgc a                              31

<210> SEQ ID NO 11
<211> LENGTH: 18
<212> TYPE: DNA
<213> ORGANISM: Drosophila acanthoptera

<400> SEQUENCE: 11
tagggataac agggtaat                                             18

<210> SEQ ID NO 12
<211> LENGTH: 18
<212> TYPE: DNA
<213> ORGANISM: Drosophila acanthoptera

<400> SEQUENCE: 12
attaccctgt tatccta                                              18

<210> SEQ ID NO 13
<211> LENGTH: 33
<212> TYPE: DNA
<213> ORGANISM: Drosophila acanthoptera

<400> SEQUENCE: 13
agcactcgag tgcgacgtga acagtgagct gta                            33

<210> SEQ ID NO 14
<211> LENGTH: 39
<212> TYPE: DNA
<213> ORGANISM: Drosophila acanthoptera

<400> SEQUENCE: 14
taccctcgag agctcgttac agtccggtgc gtttttggt                      39

<210> SEQ ID NO 15
<211> LENGTH: 34
<212> TYPE: DNA
<213> ORGANISM: Drosophila acanthoptera

<400> SEQUENCE: 15
agcagcggcc gccgaaaggg ggatgtgctg caag                           34

<210> SEQ ID NO 16
<211> LENGTH: 34
<212> TYPE: DNA
```

```
<213> ORGANISM: Drosophila acanthoptera

<400> SEQUENCE: 16
taccgcatgc gcacttagct ctaagctgac aatc                              34

<210> SEQ ID NO 17
<211> LENGTH: 21
<212> TYPE: DNA
<213> ORGANISM: Drosophila acanthoptera

<400> SEQUENCE: 17
gatccacgta cgaggcgcgc c                                            21

<210> SEQ ID NO 18
<211> LENGTH: 21
<212> TYPE: DNA
<213> ORGANISM: Drosophila acanthoptera

<400> SEQUENCE: 18
gatcggcgcg cctcgtacgt g                                            21

<210> SEQ ID NO 19
<211> LENGTH: 34
<212> TYPE: DNA
<213> ORGANISM: Drosophila acanthoptera

<400> SEQUENCE: 19
tacccgtacg cgtcttgggc tgcttacaaa cttc                              34

<210> SEQ ID NO 20
<211> LENGTH: 36
<212> TYPE: DNA
<213> ORGANISM: Drosophila acanthoptera

<400> SEQUENCE: 20
agcaggcgcg cctatgttgt gtggaattgt gagcgg                            36

<210> SEQ ID NO 21
<211> LENGTH: 22
<212> TYPE: DNA
<213> ORGANISM: Drosophila acanthoptera

<400> SEQUENCE: 21
aatttaggga taacagggta at                                           22

<210> SEQ ID NO 22
<211> LENGTH: 22
<212> TYPE: DNA
<213> ORGANISM: Drosophila

<400> SEQUENCE: 22
aattattacc ctgttatccc ta                                           22
```